United States Patent
Hartman et al.

(10) Patent No.: US 11,661,433 B2
(45) Date of Patent: May 30, 2023

(54) NEAR-IR ACTIVATABLE FLUORESCENT SMALL MOLECULES WITH DUAL MODES OF CYTOTOXICITY

(71) Applicant: VIRGINIA COMMONWEALTH UNIVERSITY, Richmond, VA (US)

(72) Inventors: Matthew Hartman, Richmond, VA (US); Koushambi Mitra, Richmond, VA (US)

(73) Assignee: VIRGINIA COMMONWEALTH UNIVERSITY, Richmond, VA (US)

(*) Notice: Subject to any disclaimer, the term of this patent is extended or adjusted under 35 U.S.C. 154(b) by 0 days.

(21) Appl. No.: 17/053,837

(22) PCT Filed: May 9, 2019

(86) PCT No.: PCT/US2019/031403
§ 371 (c)(1),
(2) Date: Nov. 9, 2020

(87) PCT Pub. No.: WO2019/217606
PCT Pub. Date: Nov. 14, 2019

(65) Prior Publication Data
US 2021/0238211 A1    Aug. 5, 2021

Related U.S. Application Data

(60) Provisional application No. 62/668,967, filed on May 9, 2018.

(51) Int. Cl.
C07F 15/00 (2006.01)
A61K 31/282 (2006.01)
A61K 41/00 (2020.01)

(52) U.S. Cl.
CPC ........ *C07F 15/0093* (2013.01); *A61K 31/282* (2013.01); *A61K 41/0042* (2013.01); *A61K 41/0057* (2013.01)

(58) Field of Classification Search
CPC ............. C07F 15/0093; C07F 23/0066; A61K 31/282; A61K 41/0042; A61K 41/0057
See application file for complete search history.

(56) References Cited

U.S. PATENT DOCUMENTS

| 2004/0023942 A1 | 2/2004 | Bart et al. |
| 2011/0263920 A1 | 10/2011 | Bourke, Jr. et al. |
| 2013/0149252 A1 | 6/2013 | Hara et al. |
| 2013/0281679 A1 | 10/2013 | Na et al. |

FOREIGN PATENT DOCUMENTS

WO    WO-2016106324 A1 *  6/2016  ......... C09B 23/0066

OTHER PUBLICATIONS

Gura (Science, v278, 1997, pp. 1041-1042). (Year: 1997).*
Ji Johnson et al. Relationships between drug activity in NCI preclinical in vitro and in vivo models and early clinical trials. British Journal of Cancer, 2001, 9 sheets. (Year: 2001).*
Freshney. Culture of Animal Cells. A manual of basic technique. Alan R. Liss, 1983, New York, p. 4. (Year: 1983).*
Dermer (Bio/Technology, 1994, 12:320). (Year: 1994).*
Levitz, Andrew R. "Synthesis of Various Classes of Cyanine Fluorophores and Their Application In In Vivo Tissue Imaging." (2017). Dissertation. Georgia State University. (Year: 2017).*
Mitra et al. Eur. J. Inorg. Chem. Oct. 2016, 1753-1763 (Year: 2016).*
Nagaya et al. Molecular Cancer Research 15.9 (2017): 1153-1162 (Year: 2017).*
Zheng, Peiming, et al. "Exosomal transfer of tumor-associated macrophage-derived miR-21 confers cisplatin resistance in gastric cancer cells." Journal of experimental & clinical cancer research 36.1 (2017): 1-13. (Year: 2017).*
Wisnovsky, Simon P., et al. "Targeting mitochondrial DNA with a platinum-based anticancer agent." Chemistry & biology 20.11 (2013): 1323-1328 (Year: 2013).*
Van Dongen, Gams et al., Photosensitizer-antibody conjugates for detection and therapy of cancer, Advanced Drug Delivery Reviews 56, pp. 31-52, 2004.
Muller, P, Photoactivatable Platinum Complexes as Potential Therapeutic Agents, Doctoral Thesis, University of Edinburgh, 2002, pp. 1-79.

* cited by examiner

*Primary Examiner* — Erin E Hirt
*Assistant Examiner* — Janice Y Silverman
(74) *Attorney, Agent, or Firm* — WCF IP

(57) ABSTRACT

Near-infrared activatable fluorescent small molecules for the photodynamic treatment of cancer are provided. Methods of treatment include contacting a plurality of cells of the cancer with a near-infrared activatable fluorescent small molecule and directing a near-IR light to the molecule for an amount of time sufficient to induce release of the active platinum species and a reactive oxygen species.

19 Claims, 12 Drawing Sheets

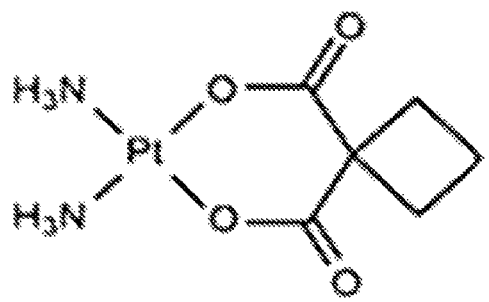
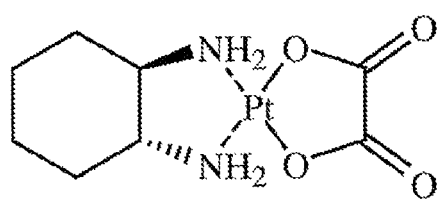
FIG. 8A
FIG. 8B
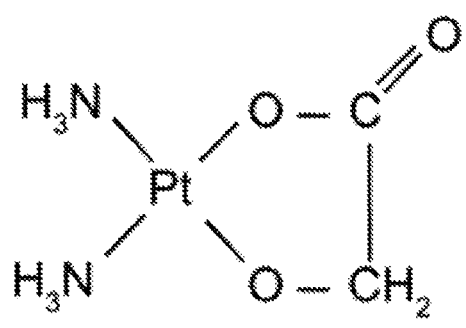
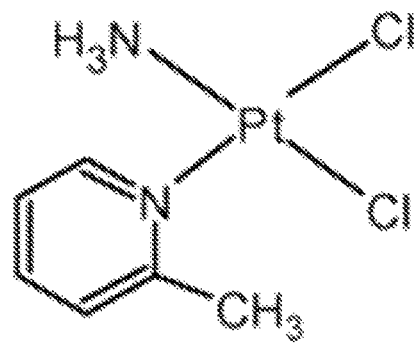
FIG. 8C
FIG. 8D

MHI-148

IR-780

IR-783

IR-808

Indocyanine green

SL-372

SL-724

SL-251

SL-370

SL-377

SL-957

SL-1046

NEAR-IR ACTIVATABLE FLUORESCENT SMALL MOLECULES WITH DUAL MODES OF CYTOTOXICITY

FIELD OF THE INVENTION

The invention is generally related to near-infrared activatable fluorescent small molecules for the photo-initiated chemotherapeutic treatment of cancer.

BACKGROUND OF THE INVENTION

The FDA validated platinum-based anticancer drugs cisplatin, oxaliplatin and carboplatin form the centerpiece of metal-based anticancer drug therapy.[1] The putative mechanism of cytotoxicity relies on an initial Pt—X (X=Cl, O) bond scission to form aquated Pt(II) species. These activated Pt(I) species can then react with nuclear DNA and form cyto-lethal Pt-DNA crosslinks ultimately leading to apoptotic cell death.[2] However, the anarchic hydrolytic behavior of these drugs leads to undesired systemic toxicity and limits the administration of higher drug-dosage levels. Controlled generation of the bioactive (aquated) form of platinum(II) drugs specifically within the targeted tumor is, therefore, an ideal way to prevent the off-target toxicity.[3] To gain control over the kinetics of metal-ligand bond rupture, Pt(IV) complexes were introduced as inert prodrugs which produce DNA damaging platinum(II) species only upon reduction by cell-abundant glutathione.[4,5] These Pt(IV) complexes showed promising tumor-targeted anticancer activities and oftentimes resulted in delivery of multiple drugs and adjuvants. Though efficacious, this strategy relies on endogenous entities for drug activation and thus the regulation of cytotoxicity is lost once the drug is administered. In another approach, platinum(II) cytotoxins were generated from photosensitive Pt(IV) diazido molecules with light.[6] The exploitation of exogenous light for uncaging "active" chemotherapeutics offers a spatio-temporal control over drug activation.[7-9] Such photo-initiated chemotherapy has advantages over clinically established photodynamic therapy (PDT), which relies on generation of cytotoxic singlet oxygen and therefore fails in the treatment of deep-seated hypoxic tumors.[10]

Recently, there have been a few successful efforts to photo-release bioactive Pt(II) species.[11a] Carboplatin and its 7-azaindole based analogues were shown to form bifunctional Pt-DNA adducts on UVA light exposure.[11b,c] Another similar example constitutes the novel Pt(II) complexes of curcumin which demonstrated visible light enhanced formation of Pt-DNA crosslinks.[11d,e] However, these approaches are limited by i) collateral tissue damage caused by UVA light and ii) the poor tissue penetration of light at these wavelengths.[8e] Thus, an ideal Pt(II) based photo-initiated chemotherapeutic agent should be activated in the "biological window" of 650-850 nm which has improved tissue compatibility and penetrating properties.[7,8e]

SUMMARY OF THE INVENTION

An aspect of the present disclosure provides a molecule comprising a cyanine scaffolded Pt(II) complex formed from a platinum-based anticancer agent and a heptamethine or pentamethine cyanine dye. In some embodiments, the anticancer agent may be cisplatin, carboplatin, oxaliplatin, nedaplatin, picoplatin, or lobaplatin. In some embodiments, the dye may be IR-797, IR-780, IR-783, IR-808, or MHI-148. The molecule may release a cytotoxic active platinum species and a reactive oxygen species when exposed to near-infrared (IR) light. In some embodiments, the molecule is linked to a tumor-targeting molecule. In some embodiments, the tumor-targeting molecule is an antibody directed against a cell-surface protein of a tumor cell.

Additional aspects of the present disclosure provide a pharmaceutical composition comprising a molecule as described herein and a pharmaceutically acceptable carrier.

Additional aspects of the present disclosure provide a method of treating a cancer in a subject in need thereof, comprising the steps of contacting a plurality of cells of the cancer with a therapeutically effective amount of a molecule as described herein and directing a near-IR light to said molecule for an amount of time sufficient to induce release of the active platinum species and a reactive oxygen species. In some embodiments, the cancer is selected from the group consisting of skin, head and neck, oral, esophageal, bladder, breast, and lung cancer, or any other types of cancer accessible with a near-IR light. In some embodiments, the reactive oxygen species is singlet oxygen. In some embodiments, a source of said near IR light is a superficial, endoscopic or bronchoscopic light source. In some embodiments, a wavelength of said near-IR light is in the range of 720-800 nm.

BRIEF DESCRIPTION OF THE DRAWINGS

FIGS. 8A-D. Exemplary anti-cancer platinum-based compounds include (A) carboplatin, (B) oxaliplatin, (C) nedaplatin, and (D) picoplatin.

DETAILED DESCRIPTION

For the purposes of the present disclosure, the terms "compound," "analog," and "molecule" stand equally well for the inventive compounds described herein, be they photodynamic or not, including all enantiomeric forms, diastereomeric forms, salts, and the like. Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Embodiments of the disclosure provide a molecule comprising a heptamethine or pentamethine cyanine scaffolded Pt(II) complex having the formula of

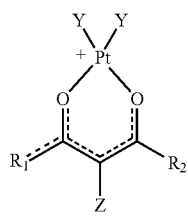

wherein X and Y are the same or different and are an unsubstituted ammine or substituted amine group or form part of a cyclic group, R$_1$ and R$_2$ are the same or different and are selected from the group consisting of H, OH, SH, sulfanyl, amine, alkyl, alkoxyl, halogen, alkenyl, alkynyl, aryl, cyano, nitro, carboxyl, carbonyl, sulfone, and sulfoxide, and Z is a heptamethine or pentamethine cyanine dye. Dashed lines indicate the presence or absence of a bond.

In some embodiments, the complex comprises one of the following structures:

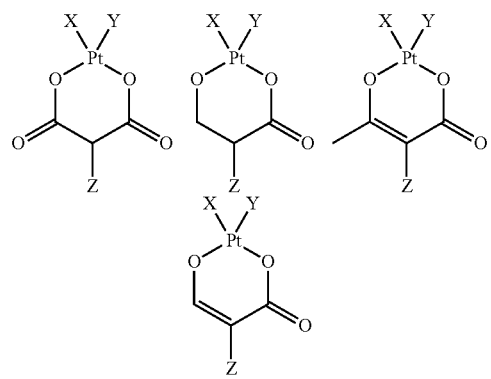

Figure 1:
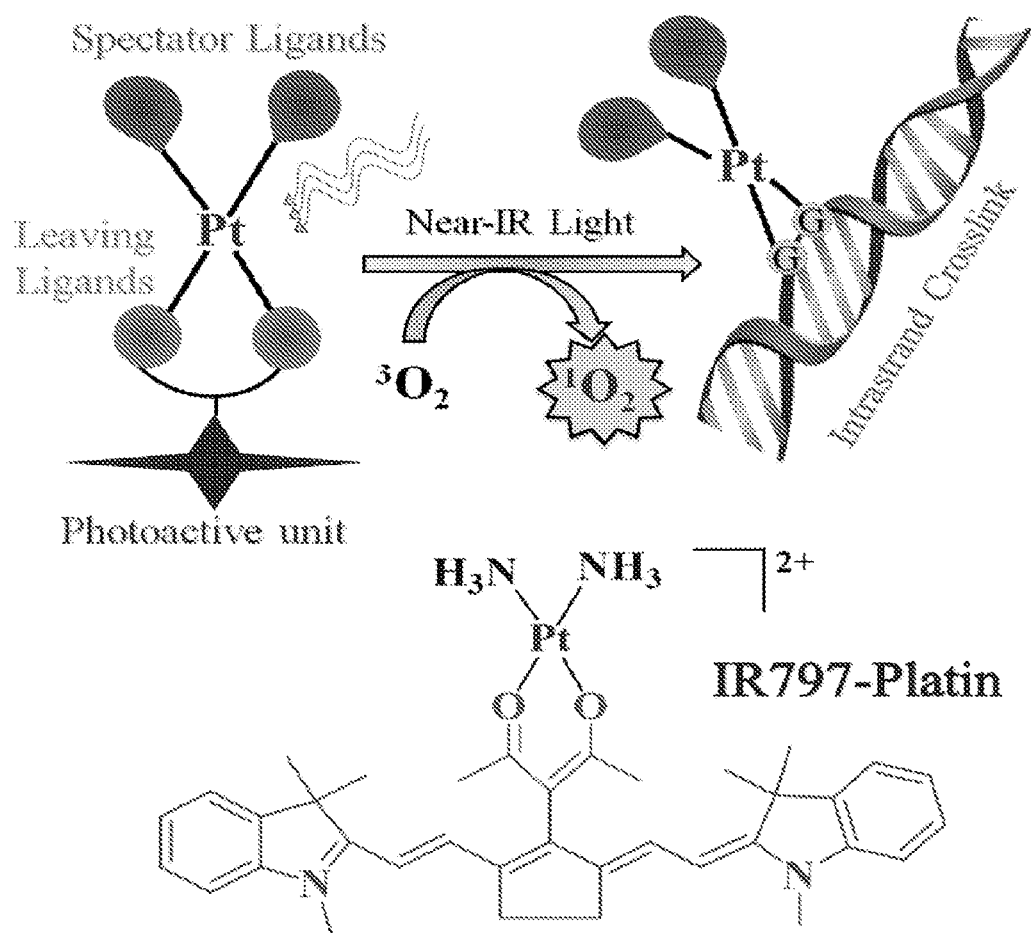
FIG. 1. Illustration of a platinum(II) complex of heptamethine cyanine, IR797-Platin which, near-IR light, induces Pt—O bond dissociation leading to enhanced DNA platination. IR797-Platin also showes significant singlet oxygen generation which results in mitochondria-targeted PDT effects in cancer cells.

The theranostic molecules describe herein comprise a platinum-based anticancer agent linked to a cyanine dye. Such molecules are activated by irradiation with near-infrared (IR) light (FIG. 1). The cyanine dye portion of the molecule fluoresces when exposed to near-IR light, thus allowing for deep tissue imaging.

The term "cyclic" refers to having an aromatic ring structure, such as pyridine, which may or may not be substituted, and may or may not include one or more heteroatoms. Cyclic structures include monocyclic structures, bicyclic structures, and polycyclic structures.

The term "sulfanyl" refers to the group —SR$_a$, where R$_a$, is substituted alkyl, substituted carbocycle, aryl, heteroaryl or heterocyclic.

The term "ammine/amine" refers to nitrogen-containing groups, such as NH$_3$, NH$_2$, and NR$^1$R$^2$, wherein R$^1$ and R$^2$ can each be independently hydrogen, alkyl, substituted alkyl, aryl, substituted aryl, and aralkyl, alkylene, arylene, aralkylene. Thus, "ammine/amine" as used herein can refer to a primary amine, a secondary amine, or a tertiary amine.

The term "alkyl" refers to a monoradical branched or unbranched saturated hydrocarbon chain preferably having from 1 to 40 carbon atoms, more preferably to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "alkoxyl" refers to a radical of —O-alkyl.

The term "halogen" or "halo" refers to, e.g. fluorine, chlorine, bromine and iodine.

The term "alkenyl" refers to straight or branched chain hydrocarbon groups of about 2 to about 20 carbon atoms, preferably about 2 to about 15 carbon atoms, and most preferably 2 to 8 carbon atoms, having, for example, about one to about four double bonds.

The term "alkynyl" refers to straight or branched chain hydrocarbon groups of about 2 to about 20 carbon atoms, preferably about 2 to about 15 carbon atoms, and most preferably about 2 to about 8 carbon atoms, having, for example, about one to about four triple bonds.

The term "aryl" refers to compounds which contain an aromatic group, e.g. a monocyclic or polycyclic aromatic compound. Monocyclic aryls generally have about 4 to about 7 carbon atoms, bicyclic aryls may have e.g. from about 7 to about 11 carbon atoms, and tricyclic aryls may contain from about 10 to about 15 or more carbon atoms. Exemplary aryls are or comprise groups that include but are not limited to: phenyl, naphthyl, biphenyl (diphenyl), thienyl, indolyl, etc. Aryls may be substituted or unsubstituted, and may or may not include one or more heteroatoms (e.g. S, N, etc.) in one or more ring structures (heteroaryls).

The term "cyano" refers to the group —CN.

The term "nitro" refers to the group —$NO_2$.

The term "carboxyl" refers to the group —COOH or salts thereof.

The term "carbonyl" refers to a divalent group of formula —(CO)—.

The term "sulfone" refers to a group —$S(O)_2R$, in which R is alkyl, aryl, or heteroaryl.

The term "sulfoxide" refers to a group —S(O)R, in which R is alkyl, aryl, or heteroaryl.

The molecules disclosed herein may provide two modes of cell-killing generated by exposure to near-IR light. The first is creation of singlet oxygen (a cytotoxic reactive oxygen species), and the second is release of a cytotoxic active platinum species. Singlet oxygen rapidly attacks any organic compounds it encounters while exemplary platinum species, such as cisplatin, act by crosslinking DNA in various different ways, in a manner that is not cell cycle specific, making it impossible for rapidly dividing cells (such as cancer cells) to duplicate their DNA for mitosis. The damaged DNA sets off DNA repair mechanisms, which activate apoptosis when repair proves impossible.

In contrast to prior photodynamic therapies, the molecules described herein do not require nanoparticle materials, such as those used for encapsulation or as carriers. In addition, near-IR light, rather than damaging UVA or blue light, is used and the cytotoxins are released in a reaction that is oxygen-independent.

Any platinum compound used for anti-cancer therapy may be incorporated into a molecule as described herein as long as the leaving ligands in the final molecule include platinum-oxygen bonds (FIG. 1). Suitable platinum compounds include, but are not limited to, cisplatin, carboplatin, oxaliplatin, nedaplatin, picoplatin, lobaplatin, satraplatin, ormaplatin, aroplatin, enloplatin, zeniplatin, sebriplatin, miboplatin, and iproplatin. A description of some of these and other suitable platinum compounds may be found in Ndagi et al. (Drug Des Devel Ther. 2017; 11:5990616). Structures of some suitable compounds are provided in FIGS. 8A-D.

Heptamethine cyanine dyes are a subclass of chemical compounds within the cyanine dye family having an absorption and fluorescence spectrum in the near-IR region. Near-IR light generally refers to light having wavelengths from 650-2500 nm. Pentamethine cyanine dyes absorb at generally shorter wavelengths, e.g. from about 650-900 nm. In some embodiments, the molecule disclosed herein is activated in the range of 650-2500 nm, e.g. 650-850 nm, 700-800 nm, or 720-740 nm. Suitable cyanine dyes include, but are not limited to, IR-797, IR-780, IR-783, IR-808, MHI-148, indocyanine dyes such as indocyanine green, Quat-Cy, SL-251, SL-1041, SL-1046, SL-372, SL-724, SL-370, SL-377, and SL-957. Other suitable dyes include those described in U.S. Pat. No. 8,889,887, US 2014/0348746, U.S. Pat. Nos. 5,973,158, and 7,504,089 incorporated herein by reference. The chemical structures of some exemplary dyes are shown in FIGS. 9A-L.

In some embodiments, the dye is such that an acetylacetone (Hacac) derivative of the dye may be synthesized from a chloro cyanine precursor. In some embodiments, chelating groups other than acetylacetone may be used, such as malonate, fluorinated or other derivatives of acac, lactol, etc.

In some embodiments, the compounds of the disclosure may be modified to improve properties such as water solubility. For example, $SO_3$ groups may be incorporated on the backbone of the heptamethine cyanine to improve water solubility, decrease dark toxicity, and/or to make the compound cell impermeable.

In some embodiments, the compounds of the disclosure are attached or linked to a cell- or tumor-targeting agent, such as a peptide or antibody. For example, the cyanine scaffold may be attached to various cell targeting moieties, such as biotin, folic acid, hyaluronic acid, etc. or to an antibody which will improve uptake and accumulation in cancer cells over normal cells. The targeting agent can be specific for a tumor cell-surface antigen, a stromal component of a tumor, an intracellular antigen or an intranuclear antigen. In some embodiments, the targeting agent binds to a tumor antigen selected from the group consisting of HER2/neu, EGFR, hepsin, Tie2, 11-6 receptor, GRP78, CD4, CD21, CD25, melanin, neuropilin, CTLA4, EphA, MMP-9, and N-cadherin. When accumulating in or around the tumor in vivo, the fluorescence properties can be used for detection of tumor margins. Furthermore, specific targeting of tumor/tumor cells allows for a higher dose of light to increase release of the platinum species and enhance formation of singlet oxygen.

The present disclosure further provides methods for preparing the compounds as described herein. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the compounds described herein.

The preparation methods described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

The present disclosure further provides photodynamic or photo-initiated methods for treating cancer. For example, a plurality of cancer cells may be contacted with a therapeutically effective amount of a molecule as described herein and a near-IR light may be directed to the molecule for an amount of time sufficient to induce release of the active platinum species and a reactive oxygen species. The molecules may be use to treat light-accessible, generally non-metastatic tumors, such as skin, oral, esophageal, bladder, breast, head and neck, and lung cancer. Treatment of other types of skin diseases is also contemplated. In some embodiments, the molecule may be used to treat any type of cancer which the platinum-based anticancer agent incorporated into the molecule is capable of treating alone. For example, molecules incorporating cisplatin may be used to treat testicular cancer, ovarian cancer, cervical cancer, breast cancer, bladder cancer, head and neck cancer, esophageal cancer, lung cancer, mesothelioma, brain tumors, and neuroblastoma.

In the context of the disclosure, the term "treating" or "treatment", as used herein, means reversing, alleviating, inhibiting the progress of, or preventing the disorder or condition to which such term applies, or one or more symptoms of such disorder or condition.

As used herein, the term "photodynamic" or "photo-initiated" treatment or therapy refers to a treatment for destroying cells or modulating immune function, including immune response, of cells and tissue through use of a drug that can be activated by light of a certain wavelength and dose.

A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the disclosure can be administered.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The methods of the disclosure involve administering compositions comprising at least one (i.e. one or more) of the compounds disclosed herein to a patient in need thereof. The present disclosure thus also provides compositions which comprise the compounds as described herein, usually together with a pharmacologically suitable carrier or diluent. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of compound in the formulations may vary. However, in general, the amount in the formulations will be from about 1% to about 99%.

The compound compositions (preparations) of the present disclosure may be administered by any of the many suitable means which are well known to those of skill in the art, including but not limited to: by injection, inhalation, orally, intravaginally, intranasally, by ingestion of a food or product containing the molecule, topically, as eye drops, via sprays, etc. In addition, the compositions may be administered in conjunction with other treatment modalities such as other agents or procedures which are used to treat cancer or the conditions which cause cancer in the patient, examples of which include but are not limited to surgical procedures, chemotherapeutic agents, radiation, immunotherapies, antibiotics, and agents that boost the immune system.

Depending on the part of the body being treated, the compounds may be injected intravenously into the diseased area or applied to the skin. After allowing time for the compound to accumulate in the tumor region, a light source is applied to the area to be treated. The source of light may be superficial, endoscopic, or bronchoscopic. In some embodiments, the light energy is applied externally, e.g. over or at the skin of the subject being treated, and wavelengths capable of penetrating the skin are transmitted there through and thus used to photocleave the prodrug molecules under or in proximity to the skin. In other embodiments, light sources may be inserted into or through a cavity of the body (mouth, urethra, esophagus, vagina, threaded through a blood vessel, etc.) or via a surgical incision in order to access tissue and/or cells that are targeted for irradiation. In some embodiments, the light source is a light-emitting diode (LED). In some embodiments, miniature LED arrays may be implanted into tissue, or placed on catheters, and moved through the body. In some embodiments, LED dice are fixed to a flexible, compact substrate.

Light exposure is generally performed from a period of time ranging from about 1 minute to several (e.g. 1, 2, 3, 4, or 5) hours, and may generally be in the range of from about 5 to about 60 minutes. Delivery of light may be continuous during the period, or may be pulsed at short intervals (e.g. a few milliseconds per pulse). Light energy in the range from about 50 to about 1000 J/cm$^2$ of light array fluence in the range from about 5 to about 50 mW/cm of light array may be delivered to the treatment site (e.g. see U.S. Pat. No. 8,235,975 to Chen et al., the complete contents of which is herein incorporated by reference). A single exposure may suffice or multiple exposures may be warranted. In some embodiments, after a single step of administering, the molecule may remain in circulation (e.g. over a period of several hours or longer), and multiple exposures may occur at timed, spaced apart intervals during that time, e.g. hourly, every few hours, etc. Alternatively, light exposure may be undertaken at various time intervals after additional steps of administration, e.g. daily, weekly, biweekly, etc., over a period of months. The details of such treatment protocols are generally developed during or taking into account the results of clinical trials, and may be modified by a skilled practitioner on a case by case basis. Guidance may be found, for example, in: Morton et al., British Journal of Dermatology 2008 159:1245-1266; and Panjehpour and Overholt, Lasers in Surgery and Medicine 2006 38:390-395.

The amount of compound that is administered is generally in the range of from about 1 to about 20 mg/kg, and preferably in the range of from about 5 to about 10 mg/kg, although as one of skill in the art will recognize, the precise amount may vary depending on one or more attributes of the drug recipient, including but not limited to: weight, overall health, gender, age, nationality, genetic history, other conditions being treated, etc.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Summary

Presented herein is a novel heptamethine cyanine scaffolded Pt(II) complex, IR797-Platin (1), which exhibits unprecedented Pt—O bond scission and enhancement in DNA platination in near-IR light. Complex 1 also displayed significant singlet oxygen quantum yield thereby qualifying as a near-IR photodynamic therapeutic agent. Complex 1 showed 30-60 fold enhancements of cytotoxicity in near-IR light in various cancer cell lines. The cellular imaging properties of 1 were also leveraged to observe its significant co-localization in cytoplasmic organelles. This is the first demonstration of a near-IR light-initiated therapy involving the cytotoxic effects of both active cisplatin and singlet oxygen.

Materials and Methods

Materials and instruments: All reactions were performed in an inert atmosphere using dry solvents and oven-dried glassware. The reactions were carried out in light-protected hoods using Al foil-wrapped glassware. All chemicals were purchased from commercial sources (Sigma Aldrich, Fisher Scientific, VWR, TCI America and Life Technologies) and were used as received. ctDNA was purchased from Sigma-Aldrich (catalog no: D1501). Complex 2 was prepared by known protocols and the characterization data matched with literature reports. $^1$H and $^{13}$C NMR spectra were recorded using either a 400 MHz Bruker Avance™ or a 300 MHz Varian spectrometer. $^1$H NMR data was reported with the following parameters: chemical shift ($\delta$), coupling constant (J) and integration values. $^{13}$C NMR data was reported in chemical shifts. Electrospray ionization (ESI-MS) and high-resolution liquid chromatography mass spectral (LC-MS) analyses were performed with "Thermo Finnigan LCQ deca XP max" mass spectrometer in positive mode ionization. Absorption and fluorescence measurements were carried out using Varian Cary Eclipse and Agilent spectrophotometers. Platinum content was measured by inductively coupled plasma mass spectrometric (ICP-MS) method using Varian ICP 820-MS instrument. High performance liquid chromatography (HPLC) purification was carried out using a Shimadzu Prominence system using Vydac (218TP C18 5µ) column using acetonitrile and water as eluents (10-100% gradient) and was monitored at 770 and 430 nm. Excited state lifetimes were measured using Zeiss 780 multiphoton microscopy equipped with a Becker & Hickl FLIM hybrid detector (HPM-100-40). The decay curves were obtained using a bi-exponential fitting model with software SPCI. All experiments were performed using HPLC purified samples which were aliquoted in DMSO and stored at −80° C. MTT assay readings were taken using a BioTek Synergy H1 hybrid 96-well plate reader. Canto—BD FACSCanto™ II Analyzer instrument, equipped with BD FACS carousel loader and 2 lasers (blue: 488 nm, red: 633 nm) helped with FACS (Fluorescence activated cell sorting) data recording.

FACSDIVA and FCSExpress 5 flow software were used for data analysis. Confocal images were acquired using LSM710 Zeiss instrument (63× magnification using oil-immersion objective). Image processing was conducted with Zen and ImageJ software. The experiments denoted as "dark" were carried out in Al foil-wrapped light protected conditions, while the experiments requiring "light" exposure was carried out using commercially available LED bulbs (720-740 nm, RapidLED, Solderless Cree XP-E Far Red Led) with an average output of (3.51.5) mW·cm$^{-2}$. The intensity measurement of the LED source was done with a Thorlabs PM100 optical power and energy meter.

Synthesis of IR797-acac: IR797 chloride (250 mg, 0.49 mmol), acetylacetone (245 μl, 2.45 mmol) and N,N-diisopropylethylamine (90 μl, 0.49 mmol) were dissolved in acetonitrile (10 mL) in a sealed vial. The dark green colored solution was heated at 70° C. on a microwave apparatus (Discover, CEM, 60 W) for 15 mins. The progress of the reaction was monitored via TLC and stopped only after full consumption of the starting dye. The reaction mixture was allowed to cool down to room temperature and dichloromethane (50 mL) was added. The organic layer was washed using saturated sodium bicarbonate solution (2×10 ml), dried over anhydrous sodium sulfate, filtered, and evaporated using a rotavac. The crude material was subjected to column chromatography using ethyl acetate (100%) and dichloromethane-methanol eluents (0-10%) to yield pure product, IR797-acac (150 mg, 50% yield). $^1$H NMR (400 MHz, CDCl$_3$): δ (ppm)=7.43-7.36 (m, 4H), 7.31 (d, J=7.4 Hz, 2H), 7.21 (t, J$_1$=J$_2$=7.2 Hz, 2H), 7.11 (d, J=8.0 Hz, 2H), 6.20 (d, J=14 Hz, 2H), 3.74 (s, 6H), 3.15 (s, 4H), 2.00 (s, 6H), 1.58 (s, 12H). $^{13}$C NMR (100 MHz, CDCl$_3$): δ (ppm)=191.42, 170.78, 144.66, 142.96, 140.71, 137.40, 128.80, 124.99, 122.04, 110.04, 103.39, 48.82, 32.53, 28.42, 23.60. ESI-MS in MeCN: m/z (expected)=533.33, m/z (observed)=533.32 [M-Cl]$^+$ (100%). The compound was readily soluble in polar solvents such as acetonitrile, methanol, chloroform, dichloromethane, dimethylsulfoxide and dimethylformamide.

Synthesis of IR797-Platin (1): Cisplatin (25 mg, 0.08 mmol) and silver nitrate (27 mg, 0.1625 mmol) were dissolved in dimethylformamide (2 mL) and stirred at room temperature in the dark. After 24 h, the solution was centrifuged and filtered to remove the white precipitate (silver chloride). To this pale yellow colored filtrate, IR797acac (50 mg, 0.08 mmol) and N,N-Diisopropylethylamine (100 μL) was added. The solution was stirred at room temperature for 6 h in the dark. The solvent was removed using a rotavac to obtain a green sticky material which was dissolved in 10 mL of methanol and precipitated by slowly adding ice-cold diethyl ether (100 mL) with continuous stirring. The solution was centrifuged to obtain a green precipitate. This dissolving-precipitating protocol was repeated to isolate a crude product, which was further subjected to HPLC chromatographic separation to obtain IR797-Platin, 1 as pure product (yield=20 mg, 0.02 mmol, 25%). $^1$H NMR (400 MHz, MeOD-d$_4$): δ (ppm)=7.45 (d, J=12 Hz, 2H), 7.38-7.32 (m, 4H), 7.20-7.16 (m, 4H), 6.01 (d, J=14 Hz, 2H), 3.53 (s, 6H), 2.93 (s, 4H), 1.67 (s, 6H). $^{13}$C NMR (100 MHz, MeOD-d$_4$): δ (ppm)=190.73, 171.47, 143.05, 140.84, 137.64, 136.57, 128.43, 124.88, 121.93, 110.42, 101.87, 42.54, 30.15, 26.80, 21.79. ESI-MS in MeOH: m/z (expected)=380.66, m/z (observed)=380.66 [M-NO$_3$—Cl]$^{2+}$ (100%). The complex was soluble in polar solvents such as acetonitrile, methanol, dimethylsulfoxide and dimethylformamide.

High performance liquid chromatography: For verifying purity, samples (25 μl in 2.5% DMSO-H$_2$O) were loaded on an analytical C18 column and gradient was maintained at 10-100 percent of MeCN—H$_2$O from 10-50 min. The absorbance was measured at different wavelengths within the range of 200-800 nm. For photolysis experiments, solution of 1 (30 μl of 100 nM in 0.01% of DMSO-PBS, irradiated for 1 min) was injected on the column and eluted using the same gradient as above. The photoproducts were observed at 770 nm and/or 430 nm and assigned by recording the mass spectra of the collected fractions.

Liquid-chromatography mass spectral experiments: Solutions of 1 and IR797-acac (100 nM in 0.01% DMSO-PBS) were used to carry out LC-MS studies. Samples were injected on a self-packed fused silica (polymicro technologies) trap column (360 micron o.d.×100 micron i.d.) with a Kasil frit packed with 5-15 micron irregular phenyl C-18 YMC packing. The trap column is connected to an analytical column (360 micron×50 micron) with a fritted tip at 5 micron or less (New Objective) packed with 5 μm phenyl C-18 YMC packing. Compounds were initially trapped and then eluted into a Thermo Finnigan LCQ deca XP max mass spectrometer (Thermo Scientific) with an acetonitrile gradient from 0% to 80% over 5 minutes at a flow rate of between 50-150 nl/min. The mass spectrometer scanned in the following sequence: a MS scan from mass 100-1000 m/z is collected, followed by a zoom scan to verify charge state, then a MS/MS scan to validate structure and placed on an exclusion list for 1 min. Integration of the extracted ion chromatogram yielded its relative abundance in the samples.

DNA bound Pt content: A 1×-PBS solution containing ctDNA (500 μM) and 1 (50 μM in 0.1% DMSO-PBS) was irradiated with near-IR light (720-740 nm) for 15, 30 and 60 mins. Another identical set was incubated in dark for comparison. After treatment, the DNA was precipitated from the solutions using 10 mL of cooled ethanol, vortexed, and collected by centrifugation. The precipitate was washed twice with cooled ethanol (5 mL) to remove soluble platinum complexes. The white fibrous precipitate was dissolved using 200 μl of conc. HNO$_3$ for 12 h and diluted with distilled water to 2% HNO$_3$-water solutions. Platinum content was measured by ICP-MS instrument. Untreated samples (DNA alone, complex alone) were kept for control. Platinum standards were made by dissolving K$_2$PtCl$_4$ in 98% aq. HNO$_3$ and used for calibration. The data along with the deviation is reported based on experiments performed in duplicate.

DNA thermal denaturation experiments: The DNA thermal denaturation experiments were performed by monitoring the absorption intensity of ct-DNA (200 μM) at 260 nm at increasing temperatures (from 40 to 90° C.), both in the absence and presence of complex 1 and IR797-acac (20 μM in 1% DMSO-DPBS solutions, pH=7.2). The experiments were performed using Agilent UV-visible spectrophotometer connected to a Peltier thermostat for temperature control. Data was recorded with increasing the temperature of the solution by 1.0° C. per min. The derivative of the melting plots gave the DNA melting temperature (Tm) of the ct-DNA. Ethidium bromide (20 μM) as a standard intercalator was used for comparison.

Calculation of singlet oxygen quantum yields by DPBF method: The singlet oxygen quantum yields were obtained following standard literature methods. To improve the stability of DPBF, the singlet oxygen quenching experiments were carried out in aerated DMF solutions. The concentration of DPBF was adjusted so as to obtain an absorbance of ~1 unit at 415 nm. To this solution, 1 or IR797-acac was added in concentrations so that the absorbance at ~790 nm was in the range 0.1-0.3 units. This ratio of DPBF and compounds ensured minimum self-quenching of singlet oxygen by the dyes. Light exposure was performed with 720-740 nm LEDs for different time intervals. The relative quantum yields of singlet oxygen generation ($\varphi_A$) were calculated by using the equation: $\varphi_A = \varphi_A^{ref}(k/k^{ref})(I_a^{ref}/I_a)$, in which $\varphi_A^{ref}$ is the singlet oxygen quantum yield for the standard (methylene blue, $\varphi_A = 0.52$), k and $k_{ref}$ are the photobleaching rate constants of DPBF, and $I_a$ and $I_a^{ref}$ are the absorption intensities (790 nm) of the compound and standard.

Theoretical calculations: The coordinates for cationic 1 and the dioxetane intermediates (P1a and P1b) were obtained from Chemcraft software by drawing the molecules. These coordinates were then optimized by density functional theory (DFT) calculations using B3LYP/LanL2DZ (for Pt atom) and 6-31+G (for C, H, N and O) and executed with G09 systems. These energy-minimized structures were computed using linear response time dependent density functional theory (TDDFT) to evaluate the electronic transitions and the spin density of the orbitals.

MTT assay: Cytotoxic profiles of the compounds were assessed in the following cell lines (passage number not exceeding 15): MCF-7 (human breast cancer) C-33 A (human cervical carcinoma) and HEK293T (transformed human kidney). Around 6000 cells were seeded in 96 well transparent flat-bottom tissue-culture plate in 200 μl of Dulbecco's Modified Eagle Medium (DMEM) containing 10% FBS (Fetal Bovine Serum) and were incubated for 24 h at 37° C. and 5% $CO_2$. We performed an initial control experiment with vehicle alone (0.1% DMSO-DMEM) on cells with different dosages of near-IR light and compared it to unexposed counterparts. The cells were unharmed by light and vehicle alone up to 45 min of photoirradiation. Cells were treated with various concentrations of 1, 2, IR797-acac, cisplatin and an equimolar mixture of IR797-acac and cisplatin in 0.1% DMSO-DMEM for 4 h or 48 h in the dark. One such plate was exposed to near-IR light for 45 min in phenol-red free DMEM (200 μl) and room temperature was maintained using a cooling system. Another identical plate was kept in dark. The plates were incubated for another 24 h in dark. Finally, MTT [3-(4,5-dimethylthiazole-2-yl)-2,5-diphenyltetrazolium bromide] (25 μl of 5 mg/ml solution in PBS) was added and incubated for 3-4 h. The absorbance of the precipitated formazan was recorded at 550 nm in DMSO. Cells treated with 0.1% DMSO-DMEM was kept as controls which represented 100% viability. The half-growth inhibitory concentration ($IC_{50}$) values were calculated by nonlinear regression analysis using GraphPad Prism5. The data is represented from two independent set of experiments, each of which was performed in triplicate.

ROS detection: Reactive oxygen species (ROS) can be quantified by measuring fluorescence intensity at 525 nm of DCF (2,7-dichlorofluorescein) which is an oxidized product of DCFDA, the diacetate analog of DCF. Human cervical cancer cells, C-33 A (seeding density ~$10^5$ cells) were plated in 6-well plates and allowed to attach for 24 h. Cells were treated with complex 1 (1 μM in 0.05% DMSO-DMEM) for 4 h in dark. DMEM was replaced with phenol-red free DMEM and cells were either irradiated (near-IR light, 45 min) or kept in dark. Cells were then treated with 0.05% trypsin for 10 min and centrifuged. The pellets were re-suspended in PBS and incubated with 1 μM DCFDA 15 min at room temperature in dark. Unstained and stained cells treated only with 0.05% DMSO were kept as control. The data were collected by FACS instrument and represented as histograms or bar diagrams from experiments done in duplicate.

Apoptosis assay: Early apoptotic cells show selective cellular internalization of AnnexinV-fluorescein isothiocyanate (FITC) dye and late apoptotic/necrotic cells are permeable to both AnnexinV-FITC and propidium iodide (PI). Dead cells are selectively stained by PI. Therefore, measuring the uptake of the dyes can quantify the amount of the cells showing an apoptotic mode of cell death. Human cervical cancer cells, C-33 A (~$10^5$ cells) were incubated with 1 (1 μM in 0.05% DMSO-DMEM) for 4 h in dark. Cells were either irradiated with near-IR light for 45 min or kept in the dark in phenol-red free DMEM. Cells were incubated overnight in 10%-DMEM-FBS, after which they were precipitated by 0.05% trypsin treatment for 10 min and collected by subsequent centrifugation. Annexin V-FITC apoptosis detection kit (Sigma Aldrich, APOAF-20T ST was used for this assay. 500 μL of 1× binding buffer was used to re-suspend the cell pellets which were then stained using Annexin V-FITC (1 μL) and PI (0.5 μL) for 10 min in dark. The fluorescence intensities were determined with FACS instrument. Cells treated with 0.05% DMSO only were used for calibrating unstained and stained cells (PI alone, AnnexinV-FITC alone, both PI and AnnexinV-FITC). The data is obtained from experiments performed in duplicate and represented as percentage population of early and late apoptotic cells.

Confocal microscopic experiments: Confocal microscopic images were recorded using LSM710 Zeiss instrument at 63× magnification. Human cervical cancer cells, C-33 A were plated on cover slips in a 12-well tissue-culture plate and allowed to attach for 24 h. They were treated with complex 1 (1 μM in 0.05% DMSO) for 4 h in the dark. The cells were washed with PBS and treated with 4,6-diamidino-2-phenylindole, dihydrochloride (DAPI, nuclear stain, 300 nM), Mito-Tracker® Green (50 nM) and Lyso Tracker® Red DND-99 (50 nM) in a stepwise protocol and washed properly to avoid non-specific staining. The cover slips were mounted on slides with a drop of Antifade Gold reagent and attached by coating the periphery using transparent nail-enamel. Cells treated with 0.05% of DMSO and stained with the dyes alone were used as control for parameter optimization and to avoid auto-fluorescence and false background signals. Multiple images were taken from duplicate samples to confirm the homogeneity in obtained results.

Pt Content in whole cells and nuclear/cytosolic fractions: Approximately, $10^6$ cells (MDA-MB-231 and C-33 A) were plated in 100 mm tissue culture treated petri dishes and allowed to attach for 24 h. Cells were then treated with complex 1 (50 μM in 0.1% DMSO-DMEM) and incubated for 4 h in C-33 A and 24 h in MDA-MB-231 in dark. Dishes were either exposed to light (720-740 nm, 15 min) or kept in dark. The cells were then allowed to incubate in dark for an additional 6 h. The cells were washed with PBS and collected as pellets by centrifugation. The untreated controls were utilized to determine the total number of cells by trypan blue method (deviation is within ±10%). For estimation of Pt in whole cell, the pellets were simply dissolved overnight in conc. $HNO_3$. The cellular fractionation was done using Thermo Fisher Scientific NE-PER™ nuclear and cytoplasmic extraction reagents following the protocol with CER-I and CER-II buffer only as specified in the kit. The obtained nuclear and cytosolic fractions were dissolved overnight in conc. $HNO_3$ and diluted to 98% aq. $HNO_3$ solutions and measured for Pt content by ICP-MS instrument along with standards.

Results and Discussion

It was reasoned that it might be possible to release a bioactive Pt(II) species from its complex with a ligand that absorbs strongly in the near-IR region. Among potential organic chromophores, the heptamethine cyanine dyes have strong near-IR absorption, are easy to access synthetically, and are widely used as imaging and PDT agents.[12,13] Moreover, these cyanine dyes accumulate preferentially in the mitochondria and lysosomes. Targeting these cytoplasmic organelles is known to overcome drug-resistance and afford improved cytotoxicity of traditionally used anticancer agents.[14,15]

Figures 3A, 3B:
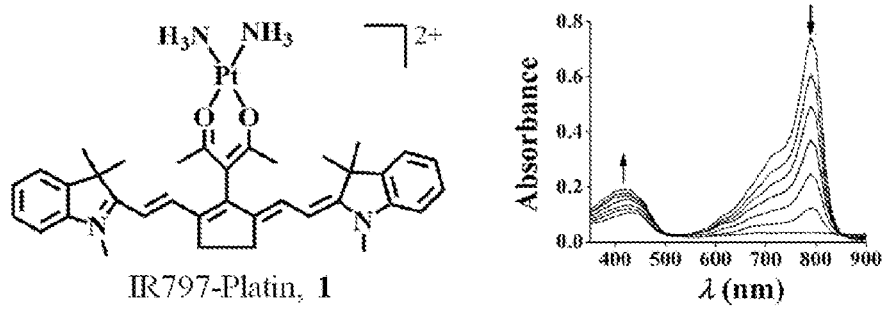
FIGS. 3A-C. (a) Chemical structure of cationic IR797-Platin, 1. (b) Absorption spectral traces of complex 1 (3 µM in 0.1% DMSO-PBS) exposed to light (readings at 30 sec and 1 min intervals) showing decrease in intensity at 790 nm and increase in intensity at 430 nm. (c) Proposed mechanism of photo-degradation of 1 when exposed to near-IR light (panel of LEDs, 720-740 nm, 3.5±1.5 mW/cm$^2$).

Based on the precedent of existing platinum(II) photoactivatable complexes,[11a] we posited that a diammine bound Pt(II) system having a photodetachable O^O bidentate donor in direct conjugation with the heptamethine cyanine framework would release an active cisplatin on near-IR light exposure. To realize our hypothesis, we successfully designed a Pt(II) conjugate of heptamethine cyanine, which we call IR797-Platin, 1 (FIG. 3A). Herein, we describe the synthesis and evaluation of photo-enhanced DNA binding properties and cellular cytotoxicity of 1.

Figure 2A:
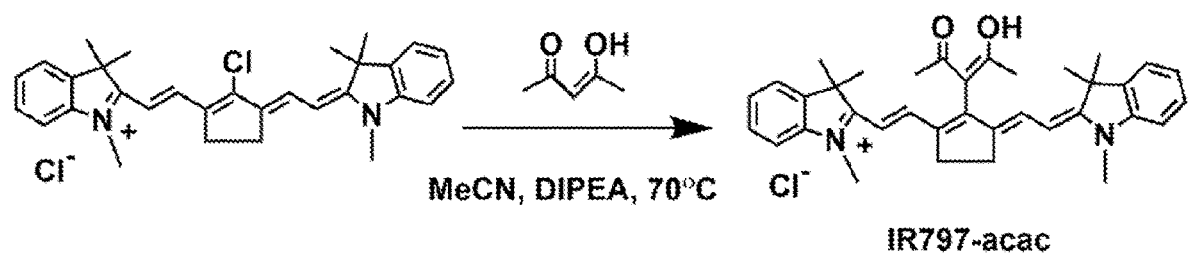
FIGS. 2A-B. Scheme showing synthesis of (A) IR797-acac and (B) complexes 1 and 2.
Figure 2B:
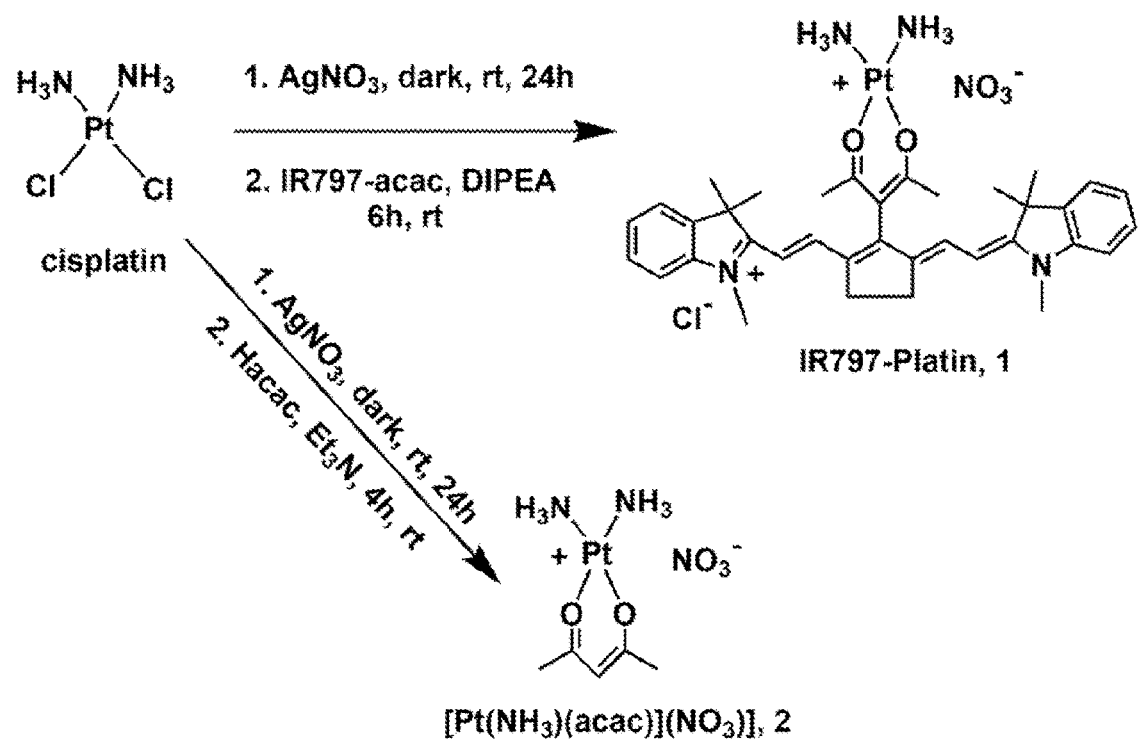

The new acetylacetone (Hacac) derivative of heptamethine cyanine, IR797-acac was successfully synthesized in one step from a chloro cyanine precursor (FIG. 2A). IR797-Platin, 1 was prepared by reacting this ligand with cisplatin after pre-activation with AgNO3 (FIG. 2B). To understand the role of the organic chromophore and light, we also prepared a cyanine-lacking analog, [Pt(NH$_3$)$_2$(acac)](NO$_3$)], 2 and used it as a control in our experiments (FIG. 2B). The newly synthesized compounds were characterized by analytical and spectroscopic techniques. $^1$H NMR spectra of 1 displayed signals assignable to the cyanine scaffold. A notable upfield shift of 0.3 ppm observed for the methyl protons of acac in 1 supported coordination of the oxygen atoms to Pt(I) center. A single mass spectra signal at m/z value of 380.6 with a Pt isotopic distribution pattern and a bi-positive charge of the fragment implicated the successful formation of 1. The purity of 1 was also verified using analytical HPLC.

Complex 1 and ligand IR797-acac showed comparable absorption profiles with a maxima at 790 nm and a high molar extinction coefficient (ε) of 4-5×10$^4$ M$^{-1}$·cm$^{-1}$. Such strong near-IR absorptions are rare for metal complexes.[8,9] It was previously noted that the N or O substitution in heptamethine cyanine dyes resulted in a large absorption blue-shift of ~100 nm.[16a,b] Interestingly, the C-substituted variants, IR797-acac and 1 retained the maximum absorbance in the near-IR region. The free ligand showed intense emission at 825 nm ($\varphi_f$=0.53) reflecting a characteristic small Stokes shift of 25 nm. Complex 1 imitated the emissive features of IR797-acac ($\lambda_{emi}$=820 nm, $\varphi_f$=0.32), but showed partial quenching due to the diamagnetic Pt(H) center.

Near-IR light-triggered uncaging of C4'-amine-substituted cyanine analogs was recently demonstrated by Schnermann and co-workers.[16] This finding, coupled with the observations suggesting that the Pt(II)-O bonds are photolabile,[11] prompted us to examine the photo-degradation pathways of 1. We performed the stability studies in solvents relevant to cell-culture settings i.e. 1% DMF or DMSO in PBS or DMEM at biological pH of 7.4. The photo reactivity of 1 and IR797-acac was demonstrated by the rapid decrease in absorbance at 790 nm and a concomitant gradual increase at 410 nm when exposed to near-IR light (FIG. 3B). The half-lives ($t_{1/2}^L$) of photodecomposition were found to be ~40 secs and 2 min for IR797-acac and 1 respectively. They exhibited considerable stability in dark conditions with $t_{1/2}^D$ of ~10 h and 20 h respectively.

Figure 3C:
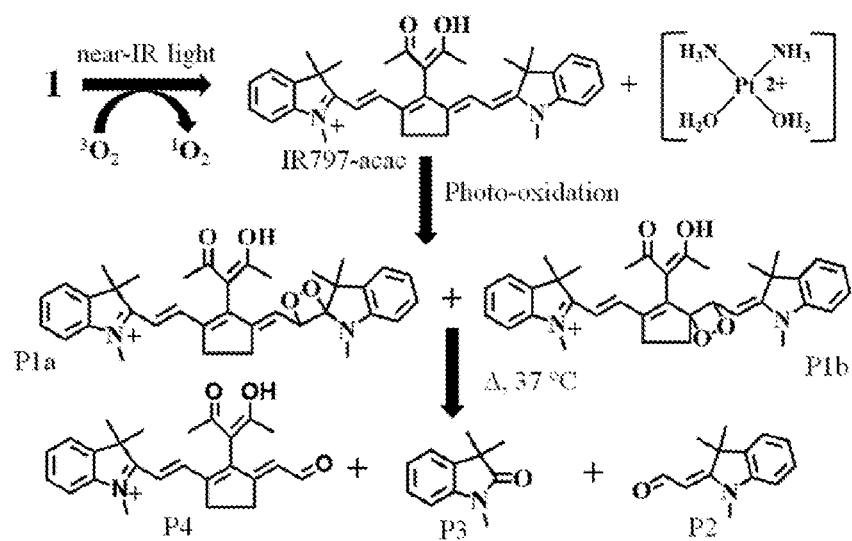

The light affected reaction course was discerned from LC-MS chromatographic elution of the photo-exposed solutions of 1 at different time intervals. To our gratification, we observed the appearance of a new signal (m/z of 533.3) which corresponds to the free ligand IR797-acac within a brief irradiation time. A portion of this photo-exposed sample when subjected to HPLC depicted the appearance of a peak which was collected and characterized as free IR797-acac. This clearly indicates the Pt—O bond in 1 rapidly dissociates and liberates the free ligand on near-IR light exposure (FIG. 3C). On further irradiation, an increase in relative counts at m/z of 565.3 was observed. This signal is attributed to the isomeric 1,2-dioxetanes, P1a and P1b and is consistent with oxidative reaction of released IR797-acac and singlet oxygen.[16b] On warming the solutions to 37° C. for 30 mins, new m/z signals at 202.2, 176.1 and 390.2 were seen which are assignable to the smaller degraded products P2-P4. Irradiation of 1 also lead to a peak of m/z 396.5 which is consistent with 1,2-dioxetane (P5a/P5b) formation. In the absence of light, 1 showed no decomposition. The accumulation and disappearance of these products over time, as discerned from a light-dose-dependent LC-MS analysis, helped us to propose the sequential photolytic scheme (FIG. 3C). $^1$H NMR studies of 1 and IR797-acac further demonstrated the formation of similar photoproducts on near-IR light exposure.[16a] The importance of singlet oxygen for degradation was confirmed from retention of absorption and emission intensity when irradiated under nitrogen atmosphere or in presence of NaN$_3$, a singlet oxygen quencher. When the same set of experiments was carried out with IR797-acac, we also observed formation of P1-P4 in accordance with the known photooxidative degradation of cyanine dyes.[16b]

Figure 4A:
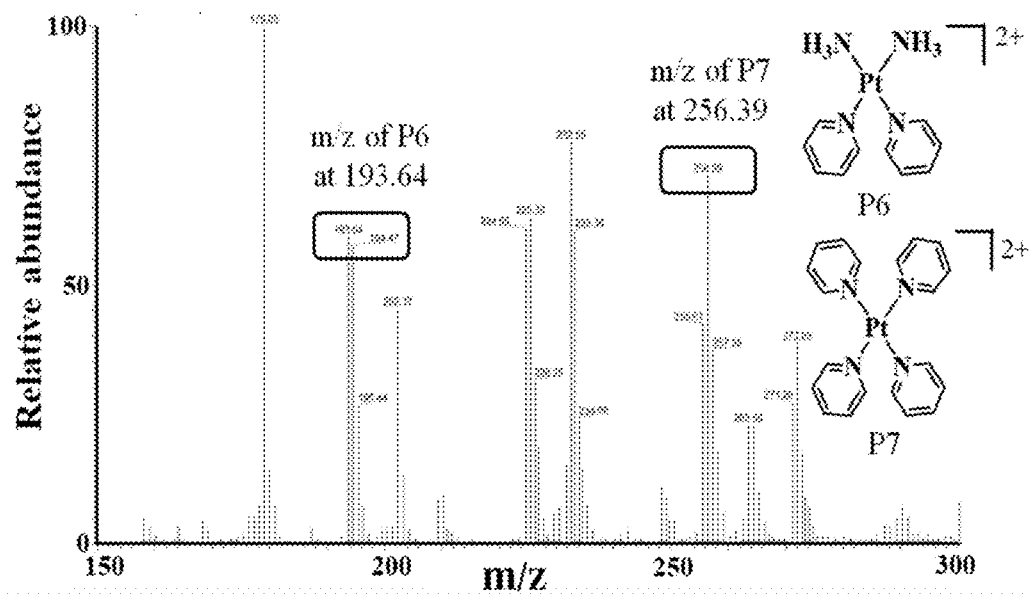
FIGS. 4A-C. (a) ESI-MS of photolysed samples of 1 and pyridine showing m/z peaks assignable to P6 and P7. (b) Decrease in absorbance of DPBF treated with complex 1 (3 µM in 0.1% DMSO-PBS) and irradiated with light of 720-740 nm (first reading at 30 s and then at intervals of 1 min). (c) Scatter plot comparing decrease in absorbance of DPBF for 1 (squares) and IR797-acac (circles) at 415 nm under similar conditions.

The widely perceived mechanism holds that "bioactive Pt(II) DNA-philes" are responsible for cisplatin cytotoxicity.[1b,2] In order to track the fate of the released Pt(II) species upon irradiation of 1, we chose to perform the release experiments in the presence of pyridine (py), a simple monodentate N donor which should trap any reactive Pt(II) species. A solution containing 1 (20 μM) and pyridine (50 μM) was exposed to near-IR light and subjected to mass spectral analysis. Predominant peaks at m/z of 193.5 and 255.5 assignable to [Pt(NH$_3$)$_2$(py)$_2$]$^{2+}$, P6, and [Pt(py)$_4$]$^{2+}$, P7, fragments were duly noted only in light exposed solutions (FIG. 4A). Formation of P6 and P7 were not observed in light-unexposed controls. The formation of these Pt-pyridine adducts therefore likely proceeded via an initial diaqua diammine Pt(R) species. These reactive Pt(II) species also formed covalent adducts with ctDNA which increased over time. ICP-MS measurements revealed enhanced platination of isolated ctDNA (2-7 ng of Pt/μM of ctDNA) when complex 1 (50 μM) was exposed to near-IR light compared to controls in the dark. As expected, we did observe slow incorporation of Pt(H) into DNA upon extended incubation of ctDNA with 1 or 2 in the dark. The DNA melting experiments and Hoechst displacement assays revealed 1 and IR797-acac interact with the minor groove of ctDNA in the dark.[17a]

Figure 4B:
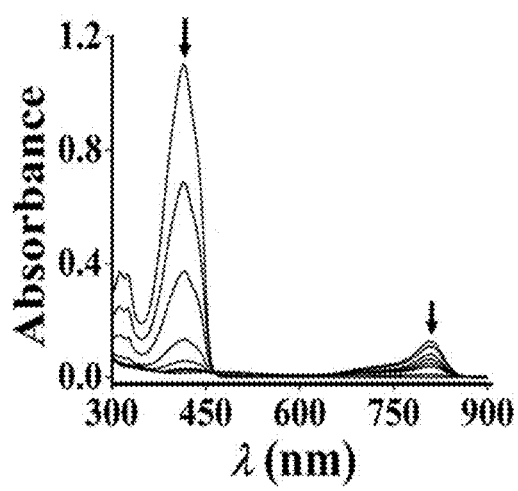
Figure 4C:
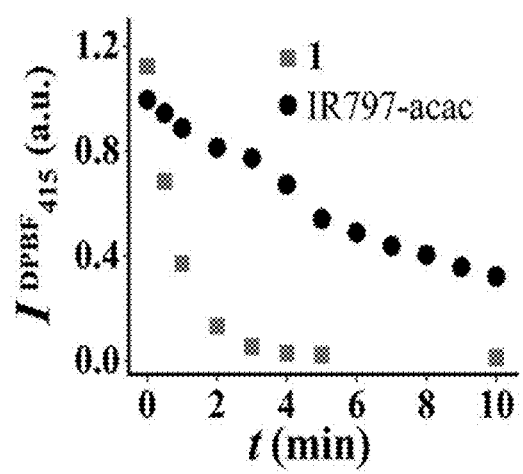

Unmodified heptamethine cyanines display poor singlet oxygen generation quantum yields.[17b] However, heavy atoms when aptly incorporated in a fluorogenic scaffold tend to increase the singlet oxygen generation via populated triplet excited states.[13b,18] The near-IR light induced rapid decrease in the absorbance of 1,3-diphenylisobenzofuran (DPBF) at 415 nm in presence of complex 1 ($t_{1/2}^{DPBF}$=30 sec, $\varphi_A$=0.15) demonstrated the generation of singlet oxygen (FIGS. 4B and 4C). In comparison, free IR797acac showed much weaker singlet oxygen production ($t_{1/2}^{DPBF}$=6 min, $\varphi_A$=0.017). Therefore, complex 1 has dual-modes of cytotoxicity through reactive Pt(II) and PDT.

Figure 5A:
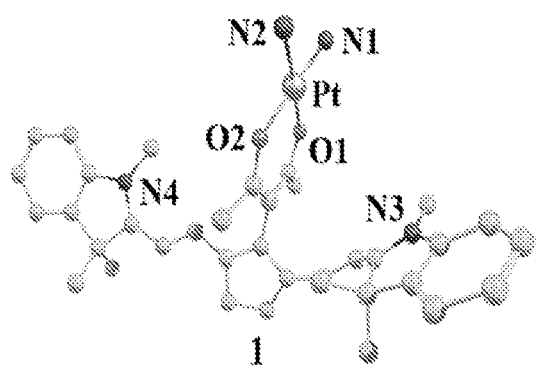
FIGS. 5A-D. Computational studies using B3LYP/LANL2DZ (for Pt) and 6-31+G (for O,N,C and H) functionals performed on 1 to obtain (a) energy-minimized structure and (b-d) the electronic distributions of molecular orbitals involved in transitions in the near-IR region. The heteroatoms are labelled and hydrogen atoms are omitted for clarity.
Figure 5B:
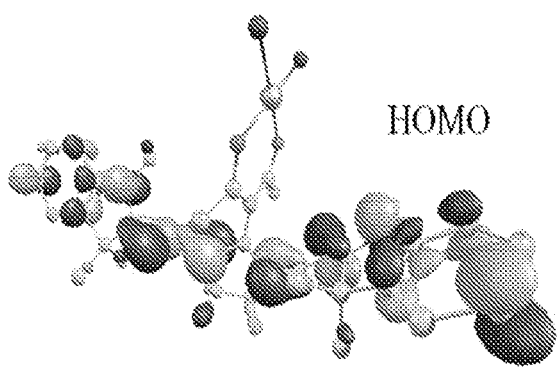
Figure 5C:
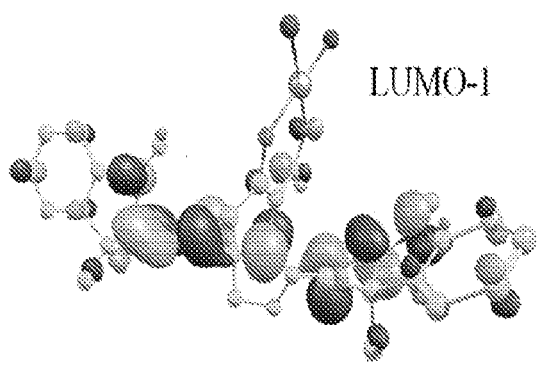
Figure 5D:
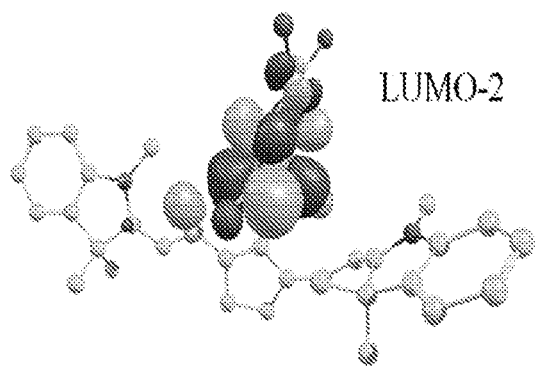

The cleavage of Pt(II)-O bonds with near-IR light is unprecedented. To better understand this process, we performed theoretical calculations. DFT (density functional theory) optimized geometry of 1 revealed a square planar Pt(II) and one of the indole rings in a parallel orientation with the acac moiety (FIG. 5A). The computed transitions showed that near-IR excitation of 1 involves charge transfer from orbitals having significant localization on both cyanine and Pt(II) (FIG. 5B-5D; Table 1). Characterization of the photo-dissociating excited triplet state depicted involvement of $d\sigma^*$ orbitals of Pt and elongation of the Pt(II)-O and Pt(II)—N bonds by ~0.15 Å in the optimized geometry. This rationalizes the observed photo-induced bond-dissociation in 1.[19] Also, predicted transitions of the 1,2-dioxetanes (P1a/P1b) resulted in weak near-IR absorption which indicates that they can only thermally degrade to form the products P2-P4.

TABLE 1

Electronic transitions of complex 1 in the red and near-IR region as predicted by TDDFT using functional B3LYP/(LANL2DZ for Pt and 6-31 + G for other atoms).

| Energy (eV) | Excited State | λ (nm) | Oscillator strength (f) | Orbitals involved (% contribution) | Nature of transition |
|---|---|---|---|---|---|
| 1.5891 | Singlet | 780.23 | 0.0755 | HOMO → LUMO + 1 (82) HOMO → LUMO (18) | LMCT |
| 1.6072 | Triplet | 771.41 | 0.0000 | HOMO → LUMO + 1 (100) | LMCT |
| 1.7885 | Triplet | 692.83 | 0.0000 | HOMO → LUMO (97) HOMO − 5 → LUMO (3) | ILCT |
| 1.9169 | Singlet | 646.81 | 1.3866 | HOMO → LUMO (78) HOMO → LUMO + 1 (17) HOMO ← LUMO (5) | ILCT |

LMCT = Ligand (cyanine) to metal (Pt(II)) charge transfer.
ILCT = Intraligand charge transfer.

Figures 6A, 6B:
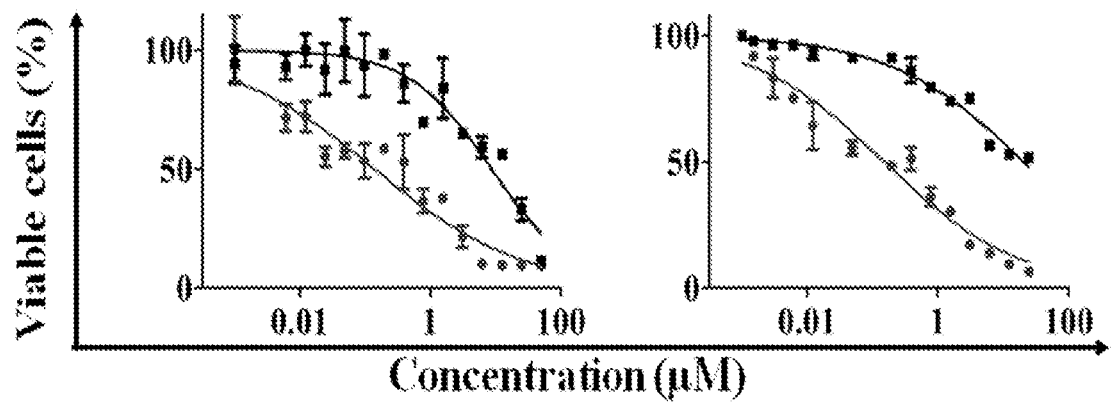
FIGS. 6A-C. Cell viability plots showing % viability as obtained in 1 treated (a) C-33 A and (b) MCF-7 cells for 4 h in dark and either photoexposed (near-IR light, 45 mins, circles) or unexposed (dark, squares) conditions. c) Confocal microscopic images in C-33 A cells showing DAPI(4',6-diamidino-2-phenylindole, nuclear stain) in 1$^{st}$ column, trackers (Mito-Tracker® Green, 1$^{st}$ row; Lyso Tracker® Red DND-99, 2$^{nd}$ row) in 2$^{nd}$ column, complex 1 in 3$^{rd}$ column and merged of all three channels in 4$^{th}$ column. The near-IR emission of complex 1 is reproduced. Scale bar=10 µm. The scatter plots show degree of overlap between images in 2$^{nd}$ and 3$^{rd}$ column. Higher Pearson correlation coefficient (P.C.C.) indicates higher co-localization.
Figure 6C:
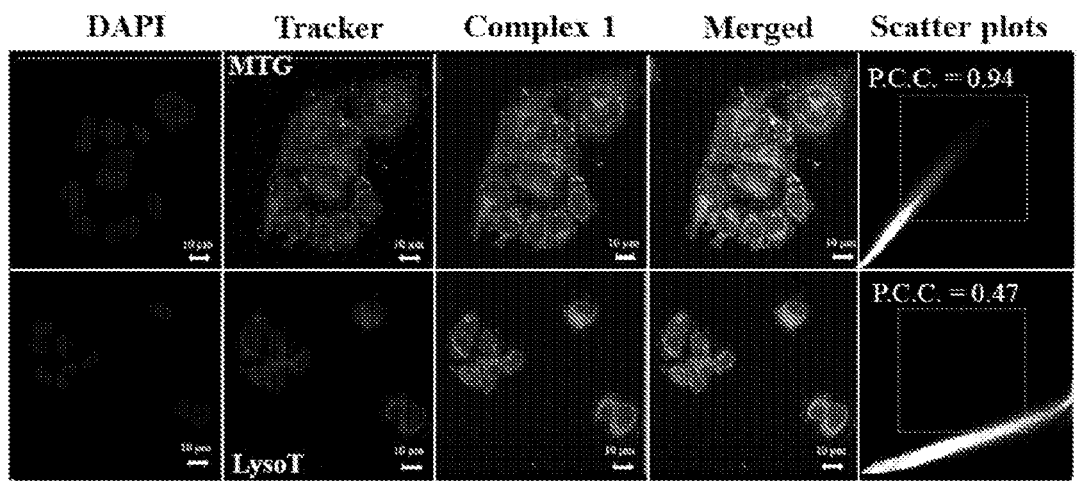

Encouraged by the ability of 1 to both produce singlet oxygen and release DNA-binding Pt(I) species in near-IR light, we next assessed the cytotoxic effects of 1 in a panel of human cancer cell lines (FIGS. 6A and 6B, Table 2). Complex 1 exhibited excellent near-IR light-mediated cytotoxicity ($IC_{50}$=0.12-2 μM) with a 30-60-fold enhancement in potency with light (FIGS. 6A and 6B, Table 2). The toxicity caused by 1 in unexposed cells was comparable to 2 and cisplatin under similar conditions. Consistent with other heptamethine cyanine dyes, IR797-acac was toxic on its own.[16b] However, neither IR797-acac alone or in combination with cisplatin showed large enhancement in potency with light. (Table 2). In light, complex 1 initiated cellular apoptosis as demonstrated by DCFDA (dichlorofluorescein diacetate) and annexinV-FITC (fluorescein isothiocyanate) assays. Confocal microscopic experiments showed notable co-localization of 1 in the mitochondria and lysosomes (FIG. 6C). This emphasizes the important role of heptamethine cyanine backbone which successfully directs 1 towards the cytoplasmic organelles. Furthermore, 1-treated and light-exposed cells had higher Pt content (quantified by ICP-MS) in the nuclear fractions as compared to dark controls. This supports light-promoted release and migration of active Pt(II) species to the nuclear DNA following a similar mechanism known for cisplatin, carboplatin and oxaliplatin.[2]

TABLE 2

$IC_{50}$ values (μM) of compounds in light and dark[a]

| Compound | C-33 A | | MCF-7 | |
|---|---|---|---|---|
| | Light[b] | Dark | Light[b] | Dark |
| Complex 1 | 0.14 ± 0.05 | 8.4 ± 1.4 | 0.65 ± 0.23 | 18.2 ± 3.2 |
| IR797-acac | 0.30 ± 0.07 | 1.2 ± 0.1 | 4.7 ± 0.8 | 5.9 ± 0.3 |
| CP[c] | 16.1 ± 1.5 | 17.7 ± 1.5 | 22.5 ± 3.2 | 25.0 ± 2.2 |
| CP + IR797-acac | 0.25 ± 0.15 | 1.4 ± 0.8 | 0.88 ± 0.17 | 2.6 ± 1.4 |

[a]Cells treated with compounds for 4 h in the dark.
[b]Cells treated with compounds for 4 h in dark and exposed to light (45 mins, 720-740 nm, 3.5 ± 1.5 mW · cm$^{-2}$).
[c]Cells incubated with cisplatin (CP) for 48 h in the dark.

In conclusion, here we demonstrate both active Pt(II)- and PDT-mediated cytotoxicity in near-IR light of a new Pt(II)-cyanine conjugate. The dual roles of platinum in triggering singlet oxygen production and bond-dissociation offer an innovative strategy for simultaneous realization of PDT and uncaging of anticancer agents. Moreover, the retention of strong absorption and emission features in the near-IR region in these C-substituted heptamethine cyanines makes them attractive theranostic agents for clinical applications. Also, the subcellular distribution of 1 is important considering the recent paradigm shift for targeting anticancer agents to cytoplasmic organelles. Our findings open up heretofore unexplored avenues of metal-based photo-chemotherapeutics offering non-surgical and externally regulated modalities for cancer treatment.

Example 2

Figure 7A:
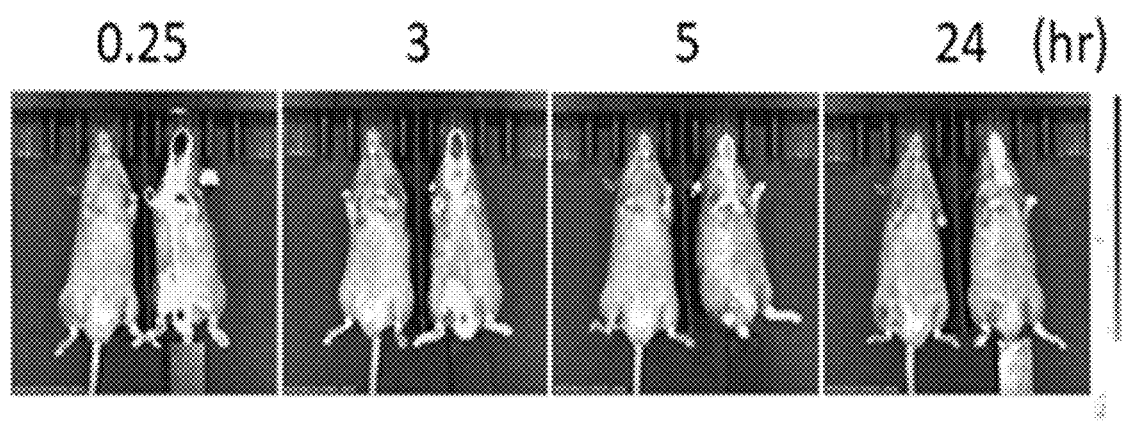
FIGS. 7A-B. Monitoring of IR797-Platin uptake. (A) One hundred microliter of Vehicle (left) or 200 nmols (7.0 mg/kg) of IR797-Platin were IV injected and the images were taken by the IVIS imager at the indicated time points. (B)#1 and #2, 20 nmols (0.7 mg/kg); #3, 0.66 nmols (0.23 mg/kg); #4, 2 nmols (0.07 mg/kg) of IR-Platin were IV injected. #1 had a <1 mm tumor and #2-4 had ~30 mm$^3$ tumors, respectively. The images were taken at the indicated times.
Figure 7B:
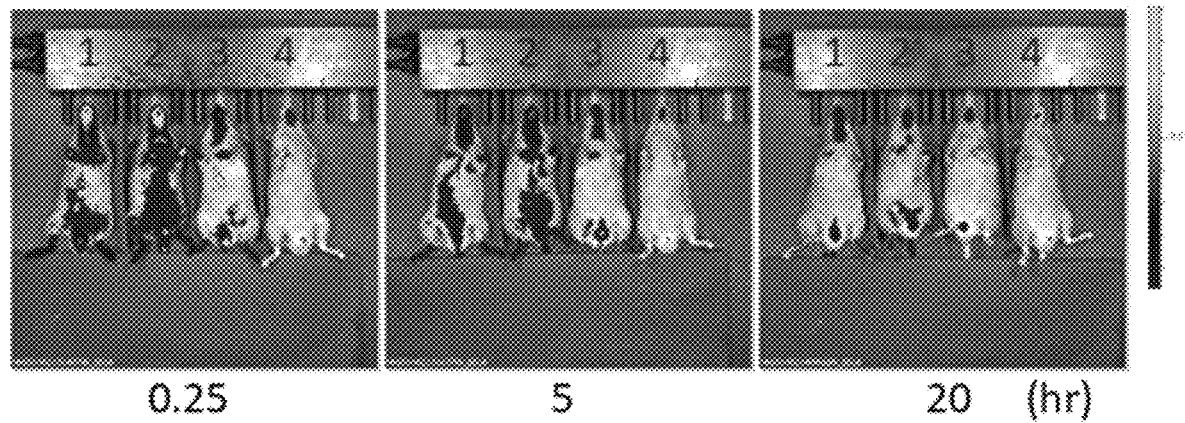
Figure 9A:
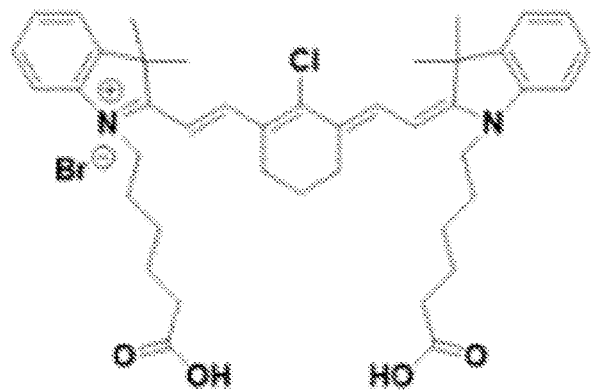
FIGS. 9A-L. Chemical structures of the following heptamethine cyanine dyes: (A) MHI-148, (B) IR-780, (C) IR-783, (D) IR-808, (E) Indocyanine green, (F) SL-372, (G) SL-724, (H) SL-251, (I) SL-370, (J) SL-377, (K) SL-957, and (L) SL-1046.
Figure 9B:
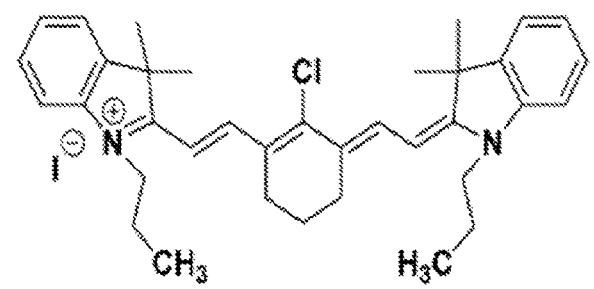
Figure 9C:
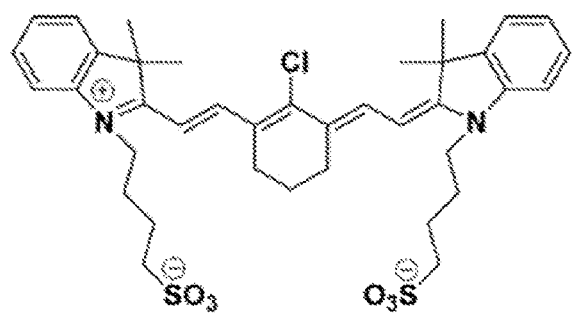
Figure 9D:
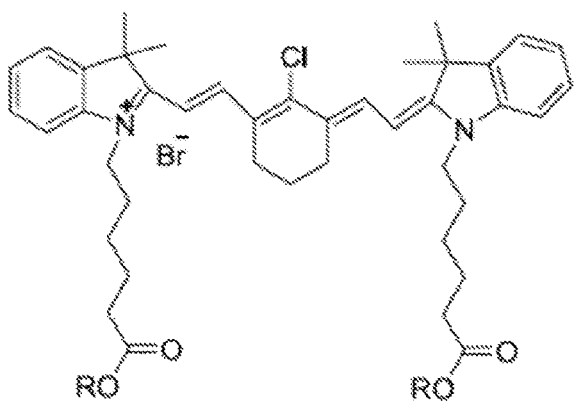
Figure 9E:
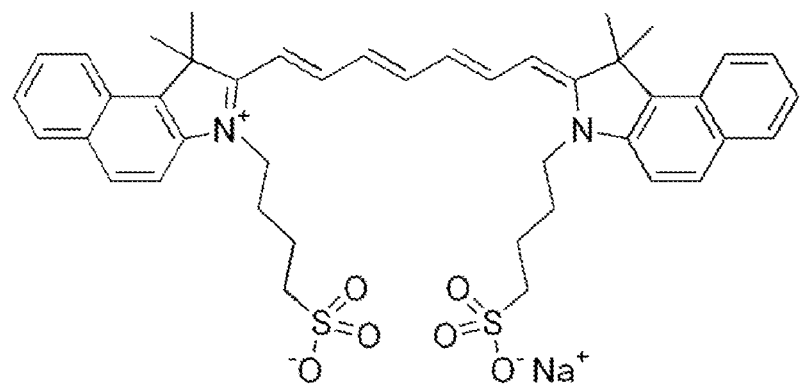
Figure 9F:
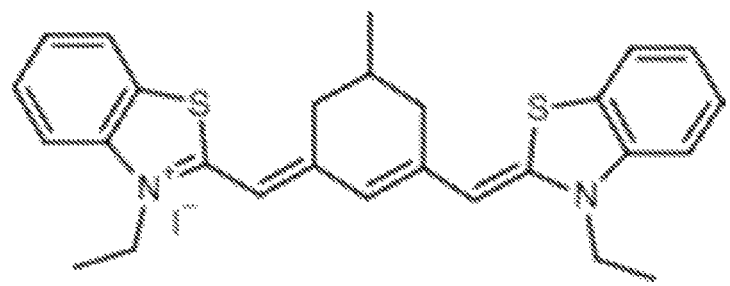
Figure 9G:
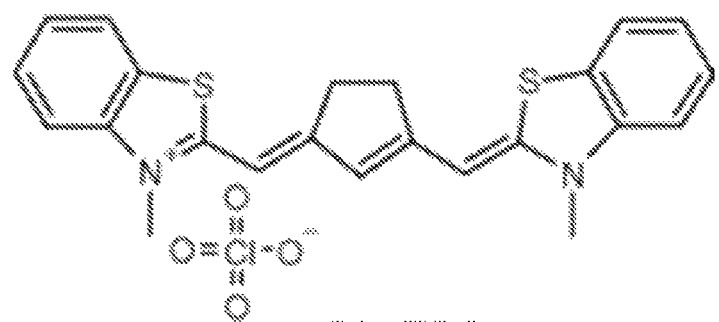
Figure 9H:
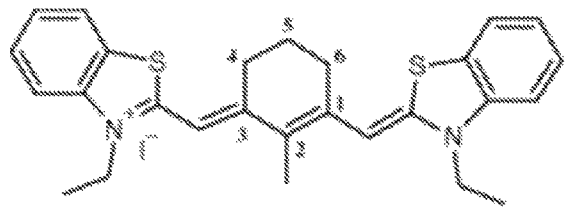
Figure 9I:
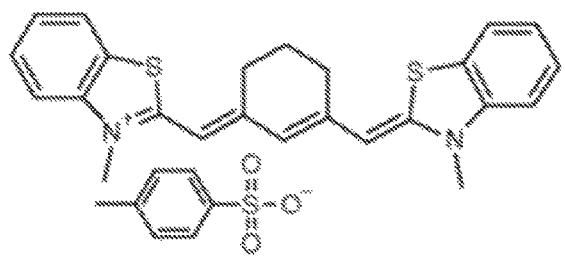
Figure 9J:
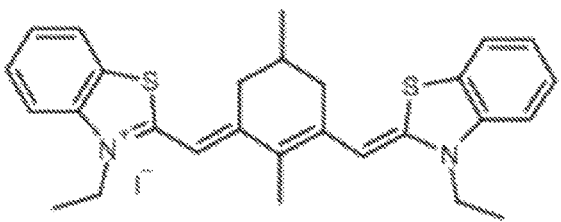
Figure 9K:
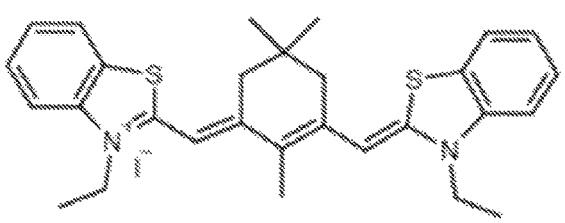
Figure 9L:
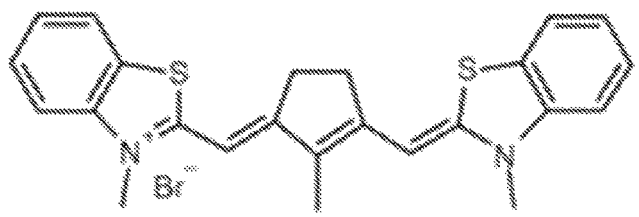

An imaging experiment with mice bearing 4NQO-induced oral tumors was conducted as shown in FIG. 7. Vehicle (10% DMSO in saline) did not show any signals (left mouse in FIG. 7A), indicating the specificity of the signals. It was also found that 20 nmols of IR797-Platin (equivalent to 0.7 mg/kg) injection could be sufficiently monitored (FIG. 7B). IR797-platin was prepared as in Example 1. At 7 mg/kg in the dark, these mice showed no signs of acute toxicity over several weeks.

Based on these data, we can inject 0.7 mg/kg of IR797-Platin in 6 mice alongside mice lacking tumors, for a total of 12 mice (8 male and 4 female, because the incidence in men is 2× vs. women) in a shorter time course (e.g. 0-8 h) to determine the time in which tumor uptake is maximized relative to normal oral tissue.

Example 3

Figure 10:
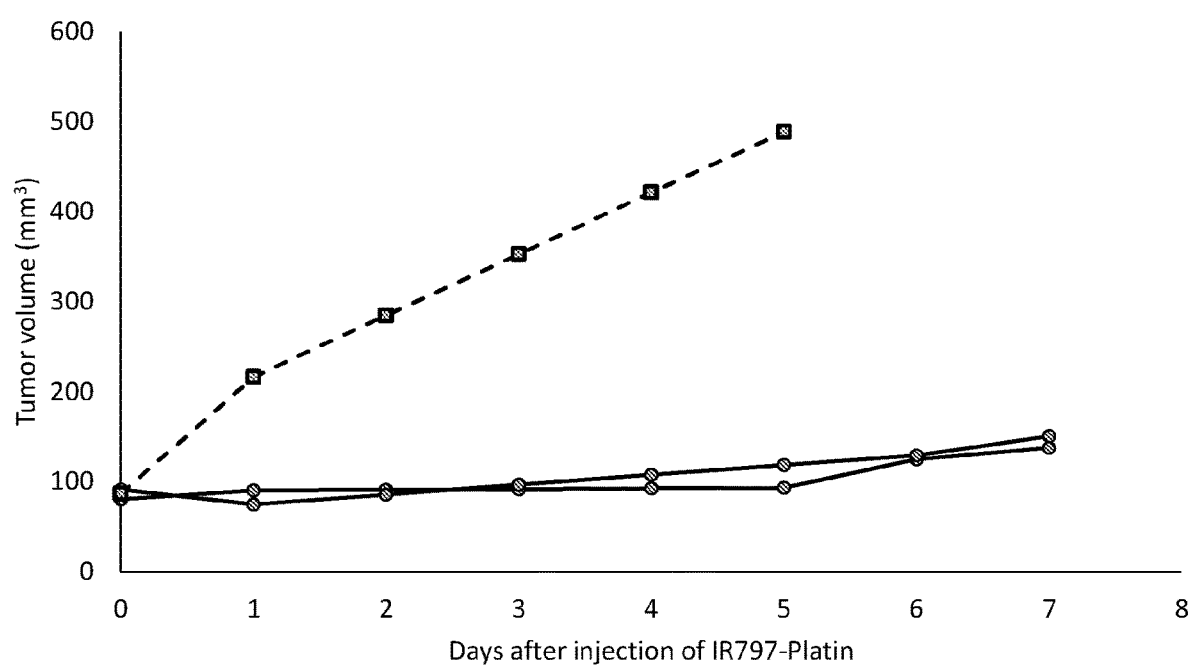
FIG. 10. Effect of IR797-Platin on tumor volume in mouse mesothelioma model after laser light illumination at a fluence of 135 J/cm2 and a fluence rate of 75 mW/cm2 (circles, solid lines) or after being kept in the dark (squares, dashed lines). Each line represents a single mouse.

The efficacy of IR797-Platin was measured in vivo. Tumor-bearing mice (AB12 mesothelioma model) were administered 6 mg/kg IR797-Platin via tail vein injection on day zero. After 1 h, laser light illumination (730 nm) was applied to the tumors for 30 minutes at a fluence of 135 J/cm$^2$ and a fluence rate of 75 mW/cm$^2$ (circles, solid lines) while control mice were maintained in ambient light (squares, dashed lines). The tumor volume for each mouse was measured over subsequent days. As shown in FIG. 10, the administration and light activation of IR797-Platin controlled tumor growth for at least 7 days after injection.

REFERENCES

[1] a) T. C. Johnstone, K. Suntharalingam, S. J. Lippard, *Chem. Rev.* 2016, 116, 3436-3486; b) P. M. Bruno, Y. Liu, G. Y. Park, J. Murai, C. E. Koch, T. J. Eisen, J. R. Pritchard, Y. Pommier, S. J. Lippard, M. T. Hemann, *Nat. Med.* 2017, 23, 461-471; c) B. W. Harper, A. M. Krause-Heuer, M. P. Grant, M. Manohar, K. B. Garbutcheon-Singh, J. R. Aldrich-Wright, *Chem. Eur. J.* 2010, 16, 7064-7077; d) K. D. Mjos, C. Orvig, *Chem. Rev.* 2014, 114, 4540-4563; e) X. Wang, X. Wang, Z. Guo, *Acc. Chem. Res.* 2015, 48, 2622-2631.

[2] a) D. Wang, S. J. Lippard, *Nat. Rev. Drug Discov.* 2005, 4, 307-320; b) D. Gibson, *Dalton Trans.* 2009, 10681-10689.

[3] a) N. Ankenbruck, T. Courtney, Y. Naro, A. Deiters, *Angew. Chem. Int. Ed.* 2018, 57, 2-33; b) S. R. MacEwan, A. Chilkoti, *Angew. Chem. Int. Ed.* 2017, 56, 6712-6733; c) R. Mahato, W. Tai, K. Cheng, *Adv. Drug Deliv. Rev.* 2011, 63, 659-670; d) F. Kratz, I. A. Müller, C. Ryppa, A. Warnecke, *ChemMedChem* 2008, 3, 20-53.

[4] a) S. G. Awuah, Y.-R. Zheng, P. M. Bruno, M. T. Hemann, S. J. Lippard, *J. Am. Chem. Soc.* 2015, 137, 14854-14857; b) Y.-R. Zheng, K. Suntharalingam, T. C. Johnstone, S. J. Lippard, *Chem. Sci.* 2015, 6, 1189-1193.

[5] a) U. Basu, B. Banik, R. Wen, R. K. Pathak, S. Dhar, *Dalton Trans.* 2016, 45, 12992-13004; b) E. Wexselblatt, E. Yavin, D. Gibson, *Angew. Chem. Int. Ed.* 2013, 52, 6059-6062; c) L. Gaviglio, A. Gross, N. Metzler-Nolte, M. Ravera, *Metallomics* 2012, 4, 260-266; d) V. Novohradsky, I. Zanellato, C. Marzano, J. Pracharova, J. Kasparkova, D. Gibson, V. Gandin, D. Osella, V. Brabec, *Sci. Rep.* 2017, 7, 3751-3064.

[6] a) P. Miller, B. Schröder, J. A. Parkinson, N. A. Kratochwil, R. A. Coxall, A. Parkin, S. Parsons, P. J. Sadler, *Angew. Chem. Int. Ed.* 2003, 42, 335-339; b) J. S. Butler, J. A. Woods, N. J. Farrer, M. E. Newton, P. J. Sadler, *J. Am. Chem. Soc.* 2012, 134, 16508-16511; c) N. J. Farrer, J. A. Woods, L. Salassa, Y. Zhao, K. S. Robinson, G. Clarkson, F. S. Mackay, P. J. Sadler, *Angew. Chem. Int. Ed.* 2010, 49, 8905-8908.

[7] a) M. M. Dcona, D. Mitra, R. W. Goehe, D. A. Gewirtz, D. A. Lebman, M. C. T. Hartman, *Chem. Commun.* 2012, 48, 4755-4757; b) M. M. Dcona, Q. Yu, J. A. Capobianco, M. C. T. Hartman, *Chem. Commun.* 2015, 51, 8477-8479; c) A. M. Goodman, O. Neumann, K. Nørregaard, L. Henderson, M.-R. Choi, S. E. Clare, N. J. Halas, *Proc. Natl. Acad. Sci. U.S.A.* 2017, 114, 12419-12424; d) M. Wegener, M. J. Hansen, A. J. M. Driessen, W. Szymanski, B. L. Feringa, *J. Am. Chem. Soc.* 2017, 139, 17979-17986.

[8] a) A. Li, C. Turro, J. J. Kodanko, *Chem. Commun.* 2018, 54, 1280-1290; b) J. K. White, R. H. Schmehl, C. Turro, *Inorg. Chim. Acta* 2017, 454, 7-20; c) L. M. Loftus, A. Li, K. L. Fillman, P. D. Martin, J. J. Kodanko, C. Turro, *J. Am. Chem. Soc.* 2017, 139, 18295-18306; d) B. S. Howerton, D. K. Heidary, E. C. Glazer, *J. Am. Chem. Soc.* 2012, 134, 8324-8327; e) W. Sun, R. Thiramanas, L. D. Slep, X. Zeng, V. Mailander, S. Wu, *Chem. Eur. J.* 2017, 23, 10832-10837.

[9] a) J. Hess, H. Huang, A. Kaiser, V. Pierroz, O. Blacque, H. Chao, G. Gasser, *Chem. Eur. J.* 2017, 23, 9888-9896; b) C. Mari, V. Pierroz, A. Leonidova, S. Ferrari, G. Gasser, *Eur. J. Inorg. Chem.* 2015, 3879-3891; c) C. Mari, V. Pierroz, S. Ferrari, G. Gasser, *Chem. Sci.* 2015, 6, 2660-2686; d) A. E. Pierri, P.-J. Huang, J. V. Garcia, J. G. Stanfill, M. Chui, G. Wu, N. Zheng, P. C. Ford, *Chem. Commun.* 2015, 51, 2072-2075.

[10] a) W. R. Wilson, M. P. Hay, *Nat. Rev. Cancer* 2011, 11, 393-410; b) H. Chen, J. Tian, W. He, Z. Guo, *J. Am. Chem. Soc.* 2015, 137, 1539-1547.

[11] a) K. Mitra, *Dalton Trans.*, 2017, 45, 19157-19171; b) J. Mcouskova, J. Stepankova, V. Brabec, *J. Biol. Inorg. Chem.* 2012, 17, 891-898; c) P. Štarha, Z. Trávníček, Z. Dvořák, T. Radošová-Muchová, J. Pracharová, J. Vančo, J. Kašpárková, *PLoS ONE* 2015, 10, e0123595; d) K. Mitra, S. Gautam, P. Kondaiash, A. R. Chakravarty, *Angew. Chem. Int. Ed.* 2015, 54, 13989-13993; e) K. Mitra, S. Gautam, P. Kondaiah, A. R. Chakravarty, *Eur. J. Inorg. Chem.* 2017, 1753-1763.

[12] a) H. Chen, B. Dong, Y. Tang, W. Lin, *Acc. Chem. Res.* 2017, 50, 1410-1422; b) E. A. Owens, M. Henary, G. E. Fakhri, H. S. Choi, *Acc. Chem. Res.* 2016, 49, 1731-1740.

[13] a) R. B. Altman, D. S. Terry, Z. Zhou, Q. Zheng, P. Geggier, R. A. Kolster, Y. Zhao, J. A. Javitch, J. D. Warren, S. C. Blanchard, *Nat. Methods* 2012, 9, 68-73; b) J. Atchison, S. Kamila, H. Nesbitt, K. A. Logan, D. M. Nicholas, C. Fowley, J. Davis, B. Callan, A. P. McHale, J. F. Callan, *Chem. Commun.* 2017, 53, 2009-2012.

[14] a) S. Fulda, L. Galluzzi, G. Kroemer, *Nat. Rev. Drug Discov.* 2010, 9, 447-464; b) S. E. Weinberg, N. S. Chandel, *Nat. Chem. Biol.* 2015, 11, 9-15.

[15] a) W. Lv, Z. Zhang, K. Y. Zhang, H. Yang, S. Liu, A. Xu, S. Guo, Q. Zhao, W. Huang, *Angew. Chem. Int. Ed.* 2016, 55, 9947-9951; b) S. Daum, M. S. V. Reshetnikov, M. Sisa, T. Dumych, M. D. Lootsik, R. Bilyy, E. Bila, C. Janko, C. Alexiou, M. Herrmann, L. Sellner, A. Mokhir, *Angew. Chem. Int. Ed.* 2017, 56, 15545-15549.

[16] a) A. P. Gorka, R. R. Nani, J. Zhu, S. Mackem, M. J. Schnermann, *J. Am. Chem. Soc.* 2014, 136, 14153-14159; b) A. P. Gorka, R. R. Nani, M. J. Schnermann, *Org. Biomol. Chem.* 2015, 13, 7584-7598; c) A. P. Gorka, M. J. Schnermann, *Curr. Opin. Chem. Biol.* 2016, 33, 117-125; d) R. R. Nani, A. P. Gorka, T. Nagaya, H. Kobayashi, M. J. Schnermann, *Angew. Chem. Int. Ed.* 2015, 127, 13839-13842.

[17] a) B. A. Armitage, *Top Curr. Chem.* 2005, 253, 55-76. b) E. M. S. Stennett, M. A. Ciuba, M. Levitus, *Chem. Soc. Rev.* 2014, 43, 1057-1075.

[18] X. Cui, J. Zhao, Z. Mohmood, C. Zhang, *Chem. Rec.* 2016, 16, 173-188.

[19] a) K. Nisbett, Y.-J. Tu, C. Turro, J. J. Kodanko, H. B. Schlegel, *Inorg. Chem.* 2018, 57, 231-240; b) L. Salassa, H. I. A. Phillips, P. J. Sadler, *Phys. Chem. Chem. Phys.* 2009, 11, 10311-10316.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A molecule, comprising a cyanine scaffolded Pt(II) complex having the formula of

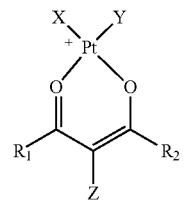

wherein X and Y are the same or different and are an unsubstituted ammine or substituted amine group or form part of a cyclic group, R$_1$ and R$_2$ are the same or different and are selected from the group consisting of H, OH, SH, sulfanyl, amine, alkyl, alkoxyl, halogen, alkenyl, alkynyl, aryl, cyano, nitro, carboxyl, carbonyl, sulfone, and sulfoxide, and Z is a heptamethine or pentamethine cyanine dye moiety linked through a carbon at a meso position in the heptamethine or pentamethine cyanine dye moiety, wherein said molecule releases a cytotoxic active platinum species and/or a reactive oxygen species when exposed to light having a wavelength in the range of 650-2500 nm.

2. The molecule of claim 1, wherein X and Y are an unsubstituted ammine group.

3. The molecule of claim 1, wherein Z is selected from the group consisting of IR-797, IR-780, IR-783, IR-808, and MHI-148.

4. The molecule of claim 1, where said molecule has the following structure

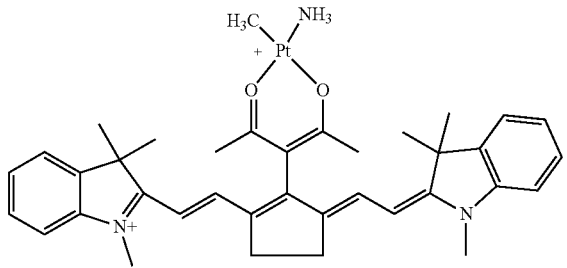

5. The molecule of claim 1, wherein the molecule is linked to a tumor-targeting molecule.

6. The molecule of claim 5, wherein said tumor-targeting molecule is an antibody directed against a cell-surface protein of a tumor cell.

7. A pharmaceutical composition comprising the molecule of claim 1 and a pharmaceutically acceptable carrier.

8. A method of treating a cancer in a subject in need thereof, wherein said cancer is susceptible to treatment with an active platinum species and/or a reactive oxygen species, comprising the steps of:

contacting a plurality of cells of the cancer with a therapeutically effective amount of a molecule according to claim 1, and directing a light having a wavelength in the range of 650-2500 nm to said molecule for an amount of time sufficient to induce release of the active platinum species and/or a reactive oxygen species.

9. The method of claim 8, wherein said cancer is selected from the group consisting of skin, oral, head and neck, esophageal, bladder, breast, and lung cancer.

10. The method of claim 8, wherein X and Y are an unsubstituted ammine group.

11. The method of claim 8, wherein Z is selected from the group consisting of IR-797, IR-780, IR-783, IR-808, and MHI-148.

12. The method of claim 8, where said molecule has the following structure

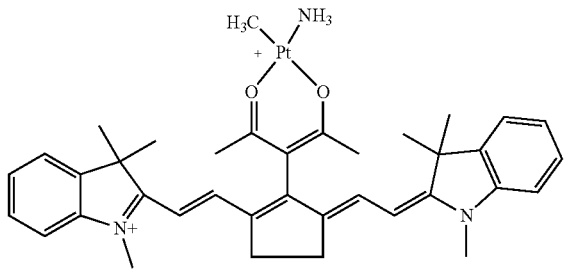

13. The method of claim 8, wherein the molecule is linked to a tumor-targeting molecule.

14. The molecule of claim 13, wherein said tumor-targeting molecule is an antibody directed against a cell-surface protein of a tumor cell.

15. The method of claim 8, wherein said reactive oxygen species is singlet oxygen.

16. The method of claim 8, wherein a source of said light is a superficial, endoscopic or bronchoscopic light source.

17. The method of claim 8, wherein a wavelength of said light is in the range of 720-800 nm.

18. The molecule of claim 1, wherein the carbon at the meso position is part of a cyclic alkenyl moiety selected from the group consisting of cyclohexene and cyclopentene.

19. A molecule, comprising a cyanine scaffolded Pt(II) complex having the formula of

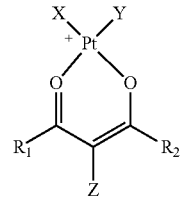

wherein X and Y are the same or different and are an unsubstituted ammine or substituted amine group or form part of a cyclic group, R$_1$ and R$_2$ are the same or different and are selected from the group consisting of H, OH, SH, sulfanyl, amine, alkyl, alkoxyl, halogen, alkenyl, alkynyl, aryl, cyano, nitro, carboxyl, carbonyl, sulfone, and sulfoxide, and Z is a heptamethine or pentamethine cyanine dye moiety linked through a carbon at a meso position in the heptamethine or pentamethine cyanine dye moiety, wherein Z is selected from the group consisting of IR-797, IR-780, IR-783, IR-808, and MHI-148.

* * * * *